US010100125B2

(12) United States Patent
Timmermand et al.

(10) Patent No.: US 10,100,125 B2
(45) Date of Patent: Oct. 16, 2018

(54) HUMANISED ANTI KALLIKREIN-2 ANTIBODY

(71) Applicant: FREDAX AB, Helsingborg (SE)

(72) Inventors: Par Oskar Vilhelmsson Timmermand, Lund (SE); Amanda Thuy Tran, Malmo (SE); Sven-Erik Strand, Lund (SE); Urpo Juhani Lamminmaki, Vanhalinna (FI); Kjell Sjostrom, Lund (SE)

(73) Assignee: Diaprost AB, Lund (SE)

( * ) Notice: Subject to any disclaimer, the term of this patent is extended or adjusted under 35 U.S.C. 154(b) by 48 days.

(21) Appl. No.: 15/036,170

(22) PCT Filed: Nov. 19, 2014

(86) PCT No.: PCT/GB2014/053420
§ 371 (c)(1),
(2) Date: May 12, 2016

(87) PCT Pub. No.: WO2015/075445
PCT Pub. Date: May 28, 2015

(65) Prior Publication Data
US 2016/0369009 A1 Dec. 22, 2016

(30) Foreign Application Priority Data

Nov. 19, 2013 (GB) .................................. 1320408.6
Feb. 5, 2014 (GB) .................................. 1401973.1

(51) Int. Cl.
| | | |
|---|---|---|
| C07K 16/40 | (2006.01) | |
| C07K 16/30 | (2006.01) | |
| A61K 51/10 | (2006.01) | |
| A61K 39/00 | (2006.01) | |

(52) U.S. Cl.
CPC .......... *C07K 16/40* (2013.01); *A61K 51/1045* (2013.01); *A61K 51/1075* (2013.01); *A61K 51/1096* (2013.01); *C07K 16/30* (2013.01); *A61K 2039/505* (2013.01); *C07K 2317/24* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahjopoulos et al. |
| 4,816,567 A | 4/1989 | Cabilly et al. |
| 5,851,451 A | 12/1998 | Takechi et al. |
| 6,326,471 B1 | 12/2001 | Kokolus et al. |
| 7,053,042 B1 | 5/2006 | Denmeade et al. |
| 2002/0001588 A1 | 1/2002 | Sinha et al. |
| 2004/0101914 A1 | 5/2004 | Pettersson et al. |
| 2004/0219163 A1 | 11/2004 | Frelinger et al. |
| 2005/0002929 A1 | 1/2005 | Sanchez-Madrid et al. |
| 2006/0182682 A1 | 8/2006 | Ulmert |

FOREIGN PATENT DOCUMENTS

| | | |
|---|---|---|
| EP | 0213303 B1 | 9/1991 |
| WO | 199821365 A2 | 5/1998 |
| WO | 200112218 A1 | 2/2001 |
| WO | 200227323 A1 | 4/2002 |
| WO | 2002098897 A2 | 12/2002 |
| WO | 2006087374 A1 | 8/2006 |
| WO | 2008070569 A2 | 6/2008 |
| WO | 2008112003 A2 | 9/2008 |
| WO | 2013061083 A2 | 5/2013 |

OTHER PUBLICATIONS

Hudson and Souriau, Nature Medicine, 2003, vol. 9, pp. 129-134.*
Hollinger and Hudson, Nature Biotechnology, 2005, vol. 23, pp. 1126-1136.*
Scott et al, Nature Reviews Cancer, 2012, vol. 12, pp. 278-287.*
Casi et al, Journal of Controlled Release, 2012, vol. 161, pp. 422-428.*
Kellof et al., "Challenges in clinical prostate cancer: role of imaging", AJR (2009) 192:1455-1470.
Leinonen et al., "Reactivity of anti-PSA monoclonal antibodies with recombinant human kallikrein-2", Tumo Biol. (1999) 20:35-37.
Magklara et al., "Decreased concentrations of prostate-specific antigen and human glandular kallikrein 2 in malignant versus nonmalignant prostatic tissue", Urology (2000) 56:527-532.

(Continued)

*Primary Examiner* — Karen A. Canella
(74) *Attorney, Agent, or Firm* — Robert C. Netter, Jr.; Dann, Dorfman, Herrell and Skillman, P.C.

(57) ABSTRACT

The present invention provides antibody polypeptides with binding specificity for human kallikrein-2 (hK2), wherein the antibody polypeptide comprises (a) a heavy chain variable region comprising the amino acid sequences of SEQ ID NO: 1 and SEQ ID NO: 2 and SEQ ID NO: 3 and/or (b) a light chain variable region comprising the amino acid sequences of SEQ ID NO: 4 and SEQ ID NO: 5 and SEQ ID NO: 6, and wherein the heavy chain variable region and light chain variable region comprise framework amino acid sequences from one or more human antibodies. The invention further provides use of said antibody polypeptides in the diagnosis and treatment of prostate cancer.

18 Claims, 20 Drawing Sheets

Figure 1:
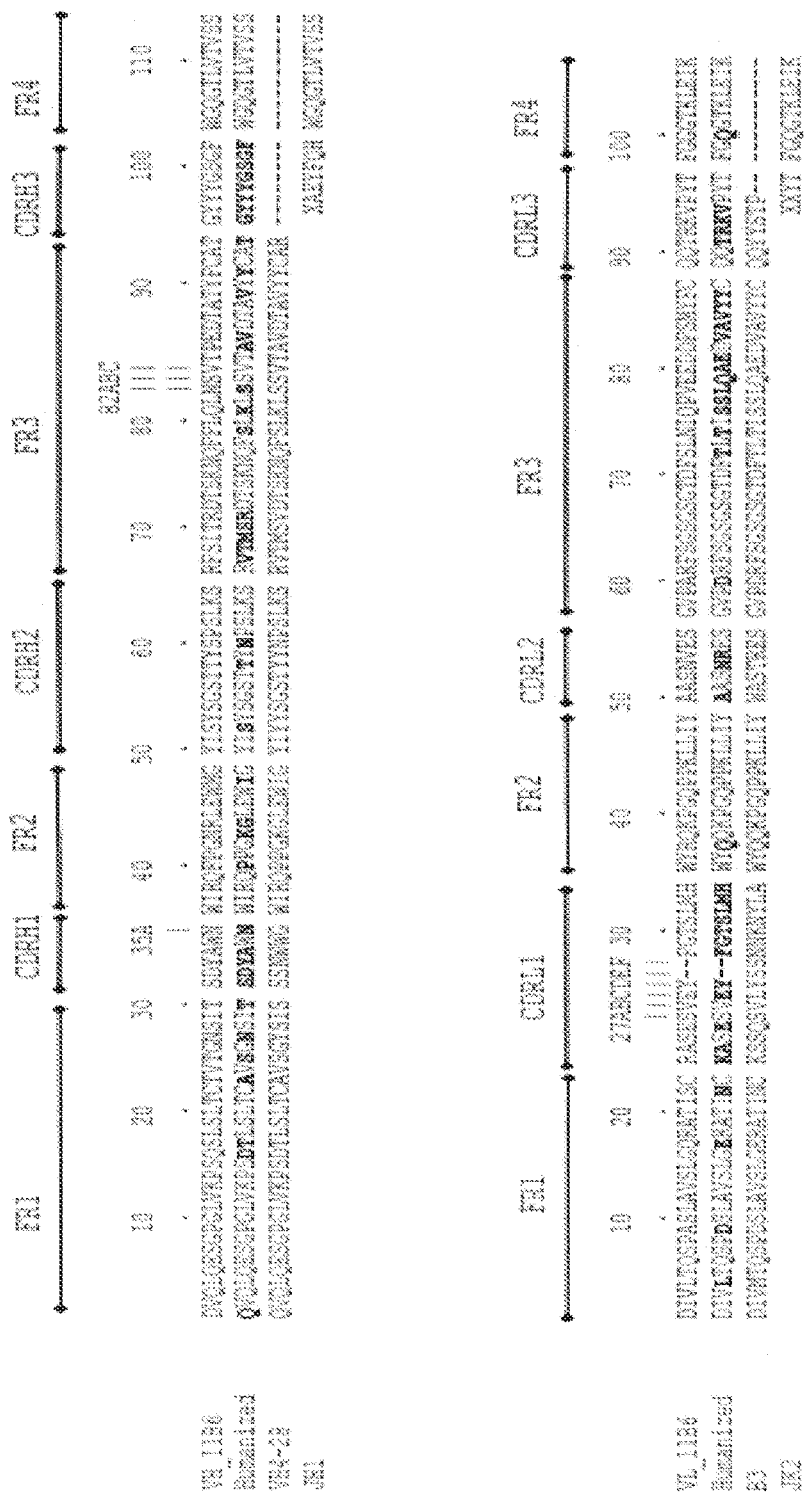

Specification includes a Sequence Listing.

(56) References Cited

OTHER PUBLICATIONS

Meyers et al., "Development of monoclonal antibody imaging of metastatic prostatic carcinoma", Prostate (1989) 14:209-220.
Nurmikko et al., "Production and characterization of novel anti-prostate-specific antigen (PSA) monoclonal antibodies that do not detect internally cleaved Lys145-Lys146 inactive PSA", Clin Chem (2000) 46:1610-1618.
Oyen et al., "Nuclear medicine techniques for the diagnosis and therapy of prostate carcinoma", Eur Urol. (2001) 40 (3):294-9.
Piironen et al., "Measurement of circulating forms of prostate-specific antigen in whole blood immediately after venipuncture: implications for point-of-care testing", Clin Chem. (2001) 47:703-711.
Schettino et al., "Impact of fusion of indium-111 capromab pendetide volume data sets with those from MRI or CT in patients with recurrent prostate cancer", Am J Roentgenol. (2004) 183:519-524.
Siivola et al., "Time-resolved fluorescence imaging for specific and quantitative immunodetection of human kallikrein 2 and prostate-specific antigen in prostatic tissue sections", Urology (2000) 56:682-688.
Stenman et al., "Summary report of the TD-3 workshop: characterization of 83 antibodies against prostate-specific antigen", Tumour Biol. (1999) 20:1-12.
Taneja et al., "Imaging in the diagnosis and management of prostate cancer", Rev. Urol. (2004) 6:101-113.
Torizumi et al., "Evaluation of Serum Prostate Specific Antigen in Diagnosis of Patients with Prostate Cancer", Radioisotopes (1991) 40:298-301.
Memari et al., "Human Tissue Kallikrein 9: Production of Recombinant Proteins and Specific Antibodies", Biol. Chem. (2006) 387:733-740.
Vaisanen et al., Abstract 374: "Sensitive Two-site Immunoassays for Measurement of the Free and Total Forms of Human Glandular Kallikrein 2 (hK2)", European Urology Supplements (2002) 1(1):96.
Angov "Codon usage: Nature's roadmap to expression and folding of proteins" Biotechnol. J. (2011) 6:650-659.
Barbas, et al., "Assembly of combinatorial antibody libraries on phage surfaces: The gene III site" Proc. Natl. Acad. Sci. USA (1991) 88:7978-7982.
Casset, et al., "A Peptide Mimetic of an anti-CD4 Monoclonal Antibody by Rational Design," Biochem. Biophys. Res. Commun. (2003) 307(1):198-205.
De Pascalis, et al., "Grafting of "Abbreviated" Complementarity-Determining Regions Containing Specificity-Determining Residues Essential for Ligand Contact to Engineer a Less Immunogenic Humanized Monoclonal Antibody" J. Immunol. (2002) 169(6):3076-3084.
ENSEMBL, Transcript: KLK2-201 (ENST00000325321), a product of gene ENSG00000167751.
GenBank Accession No. AAF08275.1.
GenBank Accession No. AAF08277.1.
Huang, et al., "A Time-Efficient, Linear-Space Local Similarity Algorithm" Adv. Appl. Math. (1991) 12:337-357.
Lilja, et al., "Prostate-Specific Antigen in Serum Occurs Predominantly in Complex with a1-Antichymotrypsin" Clin. Chem. (1991) 37(9):1618-1625.
Lovgren, et al., "Production and activation of recombinant hK2 with propeptide mutations resulting in high expression levels" Eur. J. Biochem. (1999) 266:1050-1055.
Paul, "Fundamental Immunology," 3rd Edition, Raven Press, New York (1993) pp. 292-295.
Rudikoff, et al., "Single amino acid substitution altering antigen-binding specificity" Proc. Natl. Acad. Sci. (1982) 79 (6):1979-1983.
Thompson, et al., "CLUSTAL W: improving the sensitivity of progressive multiple sequence alignment through sequence weighting, position-specific gap penalties and weight matrix choice" Nucleic Acids Research (1994) 22 (22):4673-4680.

Timmermand, et al., "Preclinical imaging of kallikrein-related peptidase 2 (hK2) in prostate cancer with a 111In-radiolabelled monoclonal antibody, 11B6" EJNMMI Research (2014) 4:51.
UniProtKB Accession No. P07288.
UniProtKB Accession No. P20151.
Veber, et al., "Conformationally restricted bicyclic analogs of somatostatin" Proc. Natl. Acad. Sci. (1978) 75 (6):2636-2640.
Almagro, et al., "Humanization of antibodies" Frontiers in Bioscience (2008) 13:1619-1633.
Almqvist, et al., "In vitro and in vivo characterization of 177Lu-huA33 A radioimmunoconjugate against colorectal cancer" Nuclear Medicine and Biology (2006) 33:991-998.
Chothia, et al., "Conformations of immunoglobulin hypervariable regions" Nature (1989) 342(6252):877-883.
Foote, et al., "Antibody Framework Residues Affecting the Conformation of the Hypervariable Loops" J. Mol. Biol. (1992) 224:487-499.
Bardies, et al., "Quantitative imaging for clinical dosimetry" Nuclear Instruments and Methods in Physics Research A (2006) 569:467-471.
Keenan, et al., "RADAR Realistic Animal Model Series for Dose Assessment" J Nucl Med (2010) 51:471-476.
Krebber, et al., "Reliable cloning of functional antibody variable domains from hybridomas and spleen cell repertoires employing a reengineered phage display system" Journal of Immunological Methods (1997) 201:35-55.
Meziere, et al., "In Vivo T Helper Cell Response to Retro-Inverso Peptidomimetics" J. Immunol. (1997) 159 (7):3230-3237.
Pajunen, et al., "Cloning, sequencing, expression and characterization of three anti-estradiol-17b Fab fragments" Biochim. Biophys. Acta (1997) 1351:192-202.
Pippin, et al., "Spectrophotometric method for the determination of a bifunctional DTPA ligand in DTPA-monoclonal antibody conjugates" Bioconjug Chem. (1992) 3(4):342-5.
Sklar, et al., "Flow cytometric analysis of ligand-receptor interactions and molecular assemblies" Annu Rev Biophys Biomol Struct. (2002) 31:97-119.
Strand, et al., "Pharmacokinetic modeling" Med Phys. (1993) 20(2 Pt 2):515-27.
Thorsett, et al., "Dipeptide mimics. Conformationally restricted inhibitors of angiotensin-converting enzyme" Biochem Biophys Res Commun. (1983) 111(1):166-71.
Tramontano, et al., "Framework residue 71 is a major determinant of the position and conformation of the second hypervariable region in the VH domains of immunoglobulins" J Mol Biol. (1990) 215(1)175-82.
Lebeau et al., "Prostate-specific antigen: an overlooked candidate for the targeted treatment and selective imaging of prostate cancer", Biological Chemistry (2010) 391(4):333-43.
Hekim et al., "Novel Peptide Inhibitors of Human Kallikrein 2", J. Biol. Chemistry (2006) 281:12555-12560.
Ulmert et al., "Imaging androgen receptor signaling with a radiotracer targeting free prostate-specific antigen", Cancer Discov. (2012) 2(4):320-7.
Evans-Axelsson et al., "Targeting Free Prostate-Specific Antigen for In Vivo Imaging of Prostate Cancer Using a Monoclonal Antibody Specific for Unique Epitopes Accessible on Free Prostate-Specific Antigen Alone", Cancer Biotherapy and Radiopharmaceuticals (2012) 27:243-251.
Anonymous, Doktorandplats i Medicinsk stralningsfysik, Internet Citation, 2010, 1-2, http://vakanser.se/jobb/doktorandplats+i+medicinsk+stralningsfysik.
Wenske et al., "Evaluation of molecular forms of prostate-specific antigen and human kallikrein 2 in predicting biochemical failure after radical prostatectomy", Int. Journal of Cancer (2009) 124:659-663.
Tremblay et al., "Immunohistochemical study suggesting a complementary role of kallikreins hK2 and hK3 (prostate-specific antigen) in the functional analysis of human prostate tumors", Am J Pathology (1997) 150:455-459.
Kim et al., "The unfolding treatment landscape for men with castration-resistant prostate cancer", Clin. Investig. (2011) 1(11):1533-44.

(56) References Cited

OTHER PUBLICATIONS

Rittenhouse et al., "Human Kallikrein 2 (hK2) and prostate-specific antigen (PSA): two closely related, but distinct, kallikreins in the prostate" Clin. Lab Sci. (1998) 35:275-368.
Van Oosten et al., "Selecting Potential Targetable Biomarkers for Imaging Purposes in Colorectal Cancer Using TArget Selection Criteria (TASC): A Novel Target Identification Tool", Translational Oncology (2011) 4:71-82.
Bolch et al., "MIRD Pamphlet No. 21: A generalized schema for radiopharmaceutical dosimetry-standardization of nomenclature", J. Nuclear Med. (2009) 50:477-484.
Bunka et al., "Aptamers come of age—at last", Nature Reviews: Microbiology (2006) 4(8):588-96.
Drabovich et al., "Selection of smart aptamers by methods of kinetic capillary electrophoresis," Anal Chem. (2006) 78(9):3171-8.
Akin et aL, "Imaging of prostate cancer", Radiol Clin North Am. (2007) 45(1):207-22.
Garkavij et al., "177Lu-[DOTA0,Tyr3] octreotate therapy in patients with disseminated neuroendocrine tumors: Analysis of dosimetry with impact on future therapeutic strategy", Cancer (2010) 116:1084-1092.
Hoppe-Seyler et al., "Peptide aptamers: powerful new tools for molecular medicine", J. Mol. Med. (2000) 78 (8):426-30.
Hsieh et al., "Expression of human prostate-specific glandular kallikrein protein (hK2) in the breast cancer cell line T47-D", Cancer Res. (1997) 57:2651-6.
Larsson et al., "Mouse S-Factors Based on Monte Carlo Simulations in the Anatomical Realistic Moby Phantom for Internal Dosimetry", Cancer Biother Radiopharm (2007) 22:438-442.
Larsson et al., "Monte Carlo calculations of absorbed doses in tumours using a modified MOBY mouse phantom for pre-clinical dosimetry studies", Acta Oncol. (2011) 50(6):973-80.
Larsson et al., "Use of Monte Carlo simulations with a realistic rat phantom for examining the correlation between hematopoietic system response and red marrow absorbed dose in Brown Norway rats undergoing radionuclide therapy with (177)Lu- and (90)Y-BR96 mAbs", Med Phys. (2012) 39(7):4434-43.
Leinonen et al., "Epitope mapping of antibodies against prostate-specific antigen with use of peptide libraries", Clin Chem (2002) 48:2208-16.
Linden et al., "Radioimmunotherapy using 131I-labeled anti-CD22 monoclonal antibody (LL2) in patients with previously treated B-cell lymphomas", Clin Cancer Res (1999) 5(10 Suppl):3287s-3291s
Ljungberg et al., "3D absorbed dose calculations based on SPECT: evaluation for 111-In/90-Y therapy using Monte Carlo simulations", Cancer Biother Radiopharm (2003) 18:99-107.
Martensson et al., "Determining maximal tolerable dose of the monoclonal antibody BR96 labeled with 90Y or 177Lu in rats: establishment of a syngeneic tumor model to evaluate means to improve radioimmunotherapy", Clin Cancer Res (2005) 11:7104s-7108s.
Minarik et al., "90Y Bremsstrahlung imaging for absorbed-dose assessment in high-dose radioimmunotherapy", J. Nucl. Med (2010) 51:1974-1978.
Nilsson et al., "Antigenic determinants of prostate-specific antigen (PSA) and development of assays specific for different forms of PSA", Brit. J Cancer (1997) 75(6):789-797.
Orlova et al., "Cellular processing of (125)I- and (111)in-labeled epidermal growth factor (EGF) bound to cultured A431 tumor cells", Nucl Med Biol. (2000) 27:827-835.
Pettersson et al., "Free and complexed prostate-specific antigen (PSA): in vitro stability, epitope map, and development of immunofluorometric assays for specific and sensitive detection of free PSA and PSA-alpha 1-antichymotrypsin complex", Clin. Chem. (1995) 41(10):1480-1488.
Segars et al., "Development of a 4-D digital mouse phantom for molecular imaging research", MOL Imaging Biol (2004) 6:149-159.
Sgouros et al., "Bone marrow dosimetry for radioimmunotherapy: theoretical considerations", J. Nucl. Med. (1993) 34:689-694.
Sjogreen et al., "The LundADose method for planar image activity quantification and absorbed-dose assessment in radionuclide therapy", Cancer Biother. Radiopharm. (2005) 20:92-97.
Sjogreen-Gleisner et al., "Dosimetry in patients with B-cell lymphoma treated with [(90)Y]ibritumomab tiuxetan or [(131)I]tositumomab", J. Nucl. Med. Mol. Imaging (2011) 55:126-154.
Skerra et al., "Alternative non-antibody scaffolds for molecular recognition", Curr Opin Biotechnol. (2007) 18 (4):295-304.
Vaisanen et al., "Intact free prostate-specific antigen and free and total human glandular kallikrein 2. Elimination of assay interference by enzymatic digestion of antibodies to F(ab')2 fragments" (2006) 78(22):7809-15.
Vaisanen et al., "Development of sensitive immunoassays for free and total human glandular kallikrein 2", Clinical Chem. (2004) 50(9):1607-1617.
Zhu et al., "Dual-label immunoassay for simultaneous measurement of prostate-specific antigen (PSA)-alpha1-antichymotrypsin complex together with free or total PSA", Clin Chem. (2003) 49:97-103.
Armstrong et al., "Biomarkers in the management and treatment of men with metastatic castration-resistant prostate cancer", Eur. Urol. (2012) 61(3):549-559.
Bapat et al., "Radioiodination of monoclonal antibody for prostate specific antigen", J. of Radioanalytical and Nuclear Chemistry (2002) 253:227-230.
Bast et al., "Translational crossroads for biomarkers", Clin Cancer Res. (2005) 11(17):6103-8.
Becker et al., "Sensitive and specific immunodetection of human glandular kallikrein 2 in serum", Clin Chem (2000) 46:198-206.
Borgono et al., "Human tissue kallikreins: physiologic roles and applications in cancer", Mol Cancer Res. (2004) 2:257-280.
Britton et al., "Prostate cancer: the contribution of nuclear medicine," BJU Int. (2000) 86:135-142.
Chengazi et al., "Imaging prostate cancer with technetium-99m-7E11-C5.3 (CYT-351)", Nucl. Med. (1997) 38:675-682.
Darson et al., "Human glandular kallikrein 2 (hK2) expression in prostatic intraepithelial neoplasia and adenocarcinoma: a novel prostate cancer marker", Urology (1997) 49:857-862.
Diamandis et al., "Human kallikrein 11: a new biomarker of prostate and ovarian carcinoma", Cancer Research (2002) 62:295-300.
Feneley et al., "Imaging with prostate-specific membrane antigen (PSMA) in prostate cancer", Prostate Cancer Prostatic Dis. (2000) 3:47-52.
Finlay et al., "Development of a dual monoclonal antibody immunoassay for total human kallikrein 2", Clin Chem, (2001) 47:1218-1224.
Fisher et al., "Generation of monoclonal antibodies specific for human kallikrein 2 (hK2) using hK2-expressing tumors", Prostate (2002) 51:153-165.
Hricak et al., "Advances in imaging in the postoperative patient with a rising prostate-specific antigen level", Seminars in Oncology (2003) 30:616-634.
Kairemo et al., "Radioimmunotherapy with 90Y-labeled monoclonal antibodies in a nude mouse ovarian cancer model", Acta Oncology (1993) 32:801-805.

\* cited by examiner (A)

(B)

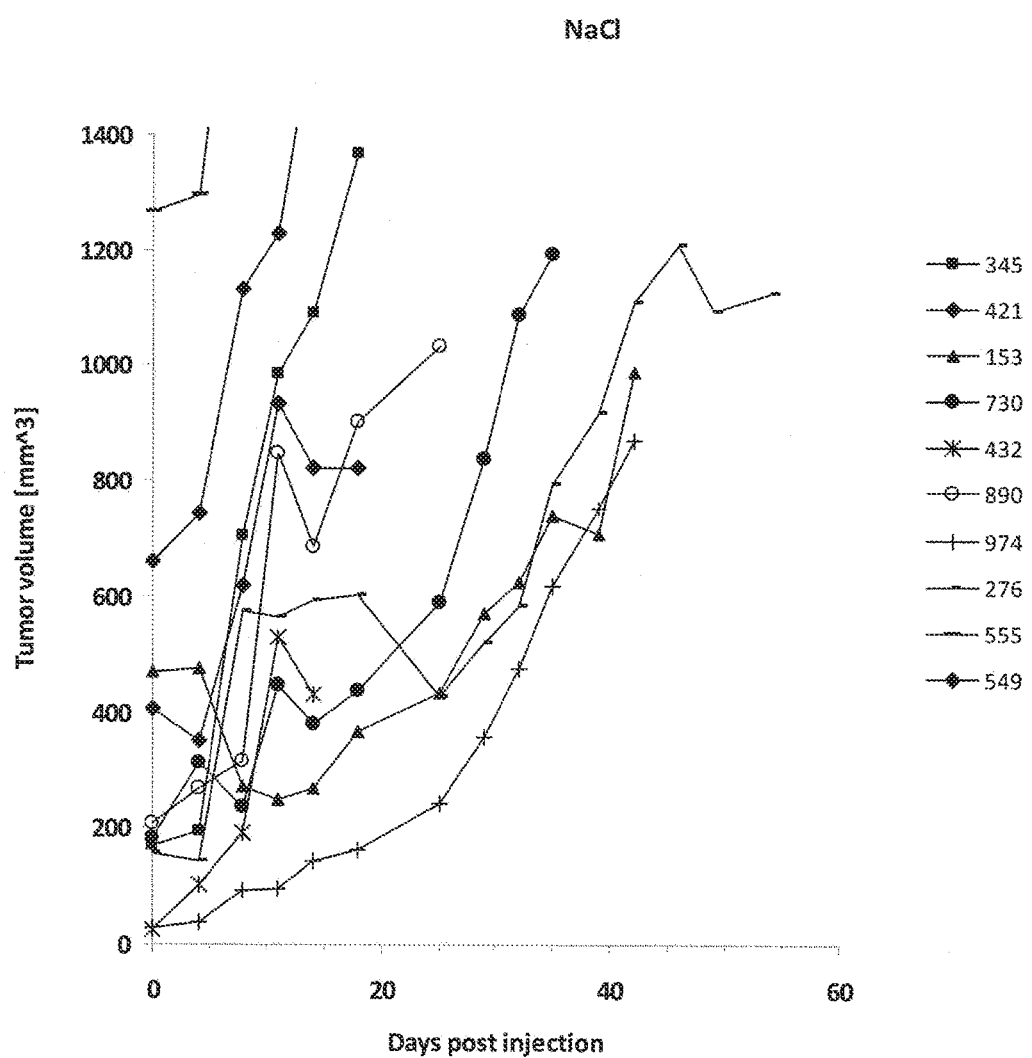

HUMANISED ANTI KALLIKREIN-2 ANTIBODY

This application is a § 371 application of PCT/GB2014/053420, filed Nov. 19, 2014, which in turn claims priority to GB Application 1320408.6, filed Nov. 19, 2013, and GB Application 1401973.1, filed Feb. 5, 2014. The entire disclosure of each of the foregoing applications is incorporated by reference herein.

FIELD OF THE INVENTION

This invention pertains in general to the field of therapeutic and diagnostic agents and methods, particularly in field of prostate cancer.

BACKGROUND

Prostate cancer is at the present time the most common form of cancer among men. The prostate is a walnut-sized gland in men that produces fluid that is a component in semen. The prostate has two or more lobes, or sections, enclosed by an outer layer of tissue. The prostate is located in front of the rectum and just below the urine bladder, and surrounds the urethra.

The occurrence of prostate cancer is highest in the northwestern part of Europe and in the United States. The growth of the tumour is usually a process that takes place during a long period of time. Prostate cancer is normally a mild form of cancer. In fact, the majority of men diagnosed with prostate cancer survive and recover, with only a minority of the men encountering a more aggressive form of prostate cancer, which metastasizes in an early stage. This aggressive form of prostate cancer may only be curable if it is diagnosed at an early stage, before the cancer has spread to extracapsular tissue.

Today, diagnosis and monitoring of prostate cancer is typically performed by measuring the concentration of a prostate specific antigen (PSA) in the blood of the patient. If the concentration of PSA is markedly high in several consecutive measurements, performed at different points of time, the assessment is that there is a probability of prostate cancer. At this point of time a biopsy may be performed to verify prostate cancer.

PSA (also known as kallikrein III) is a protein, constituted of a single chain of 237 amino acids, which is produced in the secretory cells of the prostate. These secretory cells may be found in the whole prostate gland. PSA is well established and thoroughly researched marker in respect of prostate cancer. By comparison with healthy cells the production of PSA is lower in malignant cells and higher in hyperplastic cells. It is rather contradictory that in fact the concentration of PSA is higher in blood from men suffering from prostate cancer. However, one explanation may be that the malignant cells have a deteriorated cell structure, and are therefore more permeable to PSA.

Another important serine protease suitable as a target for therapy of prostate cancer is human glandular kallikrein 2 (hK2). The gene coding hK2 is located on chromosome 19, together with the gene coding for PSA. hK2 is expressed mainly in the prostate tissue, just as PSA. In the prostate, PSA is present as an inactive pro-form and is activated through the peptidase action of hK2. Immunohistochemical research in respect of hK2 has shown that hK2 is expressed in relation to the level of differentiation. This means that hK2 is expressed in a higher yield in tissue of low differentiation, such as tissue subjected to prostate cancer, and in a lower yield in tissue of high differentiation, such as tissue subjected to benign prostatic hyperplasia (BPH) which is another common prostate problem.

Today's therapies of prostate cancer are surgery (e.g., radical prostatectomy), radiation therapy (including, brachytherapy and external beam radiation therapy, high-intensity focused ultrasound (HIFU), chemotherapy, oral chemotherapeutic drugs, cryosurgery (freezing the tumor), hormonal therapy (such as antiandrogen therapy), castration or combinations of the foregoing.

Most of these therapies (surgery and external radiation therapy) are, however, only (or primarily) useful for treatment of primary tumours and large metastases. Chemotherapy is used for disseminated of the cancer but for most of these patients, it is a palliative effect and/or prolonged survival. Other or complementary treatment modalities are therefore necessary to achieve considerable improvements of the disseminated malignant diseases, particular in cases of micrometastases.

Therapy, such as immunotherapy or radioimmunotherapy, using targeting molecules such as antibodies and fragments could give the possibility of therapy of disseminated disease.

Thus, there is a need for a new therapeutic agents and methods for treating and diagnosing prostate cancer.

SUMMARY OF THE INVENTION

Accordingly, the present invention seeks to mitigate, alleviate or eliminate one or more of the above-identified deficiencies in the art and disadvantages singly or in any combination and solves at least the above mentioned problems by providing a therapeutic agents and methods according to the appended patent claims.

A first aspect of the present invention provides an antibody polypeptide with binding specificity for human kallikrein-2 (hK2), wherein the antibody polypeptide comprises
(a) a heavy chain variable region comprising the amino acid sequences of SEQ ID NO:1 and SEQ ID NO:2 and SEQ ID NO:3

```
CDRH1:
                                          SEQ ID NO: 1
SDYAWN

CDRH2:
                                          SEQ ID NO: 2
YISYSGSTTYNPSLKS

CDRH3:
                                          SEQ ID NO: 3
GYYYGSGF
``` and/or
(b) a light chain variable region comprising the amino acid sequences of SEQ ID NO:4 and SEQ ID NO:5 and SEQ ID NO:6

```
CDRL1:
                                          SEQ ID NO: 4
KASESVEYFGTSLMH

CDRL2:
                                          SEQ ID NO: 5
AASNRES

CDRL3:
                                          SEQ ID NO: 6
QQTRKVPYT
``` and wherein the heavy chain variable region and light chain variable region comprise framework amino acid sequences from one or more human antibodies.

The above six amino acid sequences represent the complementarity-determining regions (CDRs) of the antibody polypeptides of the invention, as defined according to Kabat et al., (1991) *Sequences of Immunological Interest*, 5th edition, NIH, Bethesda, Md. (the disclosures of which are incorporated herein by reference).

By "antibody polypeptide" we include substantially intact antibody molecules, single chain antibodies, diabodies, bispecific antibodies, antibody heavy chains, antibody light chains, homodimers and heterodimers of antibody heavy and/or light chains, as well as antigen binding fragments and derivatives of the same.

The term "amino acid" as used herein includes the standard twenty genetically-encoded amino acids and their corresponding stereoisomers in the 'D' form (as compared to the natural I' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides as defined herein comprise or consist of L-amino acids.

The antibody polypeptides of the invention exhibit specificity for hK2.

An exemplary hK2 sequence is described as Transcript: KLK2-201 (ENST00000325321), a product of gene ENSG00000167751, as given in the ensemble database which can be found at the following world-wide-web address at:
 ensembl.org/Homo_sapiens/Transcript/
  Sequence_Protein?g=ENSG00000167751; r=19: 51376689-51383822; t=ENST00000325321
and has the following sequence:

```
                                        [SEQ ID NO: 7]
MWDLVLSIAL SVGCTGAVPL IQSRIVGGWE CEKHSQPWQV

AVYSHGWAHC GGVLVHPQWV LTAAHCLKKN SQVWLGRHNL

FEPEDTGQRV PVSHSFPHPL YNMSLLKHQS LRPDEDSSHD

LMLLRLSEPA KITDVVKVLG LPTQEPALGT TCYASGWGSI

EPEEFLRPRS LQCVSLHLLS NDMCARAYSE KVTEFMLCAG

LWTGGKDTCG GDSGGPLVCN GVLQGITSWG PEPCALPEKP

AVYTKVVHYR KWIKDTIAANP
```

(wherein the sequence of the mature, active hK2 protein is underlined, which is preceded at its N-terminus by a signal peptide and propeptide sequence)

Most of the hK2 found in seminal plasma is inactive and complexed with protein C inhibitor (PCI). It is also possible that hK2 forms complexes with other extracellular protease inhibitors. In vitro studies show that hK2 may bind to α2-antiplasmin (α2-AP), ACT, AMG, anti-thrombin III (ATIII), C1-inactivator and plasminogen activator inhibitor-1 (PAI-1).

In one embodiment, the antibody polypeptide has specificity for the free (that is, non-complexed) isoform of hK2 compared to the complexed isoform of hK2. Binding moieties with specificity for the free isoform of hK2 may have binding specificity for an epitope that is exposed on the free isoform of hK2, but is unexposed on the complexed isoform of hK2, and this may be a linear or a conformational (that is, non-linear) epitope. For example, the antibody polypeptide may have specificity for an epitope that includes one or more amino acid residues that are part of the catalytic cleft of hK2 that is exposed in free hK2 and unexposed in a complexed isoform, such as the form present in seminal fluid when hK2 is complexed to PCI. Epitope mapping of hK2 is described in Väisänen et al, *Clinical Chemistry* 50:9, 1607-1617 (2004), the disclosures of which are incorporated herein by reference.

Further examples of hK2 proteins are identified by the following accession numbers:
 (a) GenBank: AAF08277.1;
 (b) GenBank: AAF08275.1; and
 (c) UniProtKB/Swiss-Prot: P20151.1

The production of recombinant hK2 is described in Lovgren et al., 1999, *Eur. J. Biochem.* 266:1050-5 (the disclosures of which are incorporated herein by reference).

By "specificity" we mean that the antibody polypeptide is capable of binding to hK2 in vivo, i.e. under the physiological conditions in which hK2 exists within the human body. Preferably, the antibody polypeptide does not bind to any other protein in vivo.

Such binding specificity may be determined by methods well known in the art, such as ELISA, immunohistochemistry, immunoprecipitation, Western blots and flow cytometry using transfected cells expressing hK2. Advantageously, the antibody polypeptide is capable of binding selectively to hK2, i.e. it bind at least 10-fold more strongly to hK2 than to another proteins (in particular, other kallikreins such as prostate specific antigen or PSA). Preferably, the antigen polypeptide does not bind PSA in vivo.

Murine antibodies with specificity for hK2 are known in the art. For example, Väisänen et al., 2004, *Clinical Chemistry* 50(9):1607-1617 describes the production of monoclonal antibodies in mice with specificity for hK2 (the disclosures of which are incorporated herein by reference). Two of the antibodies, designated "11B6" and "7D7", are stated to be selective for hK2.

The amino acid sequences of the component heavy and light chains of the murine antibody 11B6 are disclosed in International Patent Application No. PCT/GB2012/052675 (WO 2013/061083; the disclosures of which are incorporated herein by reference in their entirety); see, in particular, SEQ ID NOs: 4 and 5 therein.

The antibody polypeptides of the present invention are based on a selected humanised version of the 11B6 antibody, which exhibits unexpected favourable properties.

In particular, the humanised antibodies of the invention exhibit an enhanced therapeutic ratio compared to the parent murine 11B6 antibody (m11B6) from which their CDR sequences were derived (see Example 6).

By "enhanced therapeutic ratio" we mean that the antibody polypeptide of the invention (a humanised form of the 11B6 antibody), when administered to a patient with a prostate tumour, provides a higher ratio of tumour absorbed dose to (healthy) bone marrow absorbed dose than the parent murine 11B6 antibody (compared at the same radioactivity and administration route). The ratio of tumour to bone marrow absorbed doses may be calculated using the method described in Example 6.

The unexpectedly better therapeutic profile of the antibodies of the invention permits higher radiation doses (absorbed doses) to be used, leading to greater efficacy in the treatment of prostate cancer without increasing side-effects or 'collateral damage' to healthy tissues and organs.

Humanisation (also called reshaping or CDR-grafting) is a technique for reducing the immunogenicity of monoclonal antibodies from xenogeneic sources (commonly, from rodents such as mice) and for improving their activation of the human immune system (see review by Almagro & Fransson, 2008, *Frontiers in Bioscience* 13:1619-1633; the disclosures of which are incorporated herein by reference). There are several humanised monoclonal antibodies in clinical trials and a few have been given approval to be used as drugs. Although the mechanics of producing the engineered monoclonal antibody using the techniques of molecular biology are relatively straightforward, simple grafting of the rodent complementarity-determining regions (CDRs) into human frameworks does not always reconstitute the binding affinity and specificity of the original monoclonal antibody. In order to humanize an antibody, the design of the humanised antibody is a critical step in reproducing the function of the original molecule.

The design of a humanised antibody includes several key choices, including the extents of the CDRs to be used and the human frameworks to be used. However, in order to retain the specificity of the parent antibody, it may also be critical to substitute one or more residues from the rodent mAb into the human framework regions (so-called backmutations). Identifying the position of the necessary backmutations requires a detailed sequence/structural analysis. Recently, phage libraries have been used to vary the amino acids at chosen positions. Similarly, many approaches have been used to choose the most appropriate human frameworks in which to graft the rodent CDRs. Early experiments used a limited subset of well-characterised human monoclonal antibodies (often where the structure was available), irrespective of the sequence identity to the rodent monoclonal antibody (the so-called fixed frameworks approach). Some groups use variable regions with high amino acid sequence identity to the rodent variable regions (homology matching or best-fit); others use consensus or germline sequences while still others select fragments of the framework sequences within each light or heavy chain variable region from several different human monoclonal antibodies. There are also approaches to humanisation developed which replace the surface rodent residues with the most common residues found in human monoclonal antibodies ("resurfacing" or "veneering") and those which use differing definitions of the extents of the CDRs.

However, despite extensive study of antibody humanisation, some rodent monoclonal antibodies have proved difficult to humanise.

Development of the antibody polypeptides of the invention required backmutations not only in the framework regions but also in some of the CDRs (see Example 1 below). Thus, the six CDR sequences represented above in SEQ ID NOS: 1 to 6 are derived from the murine anti-hK2 antibody 11B6, but contain mutations in CDRH2 (SEQ ID NO: 2) and CDRL1 (SEQ ID NO: 4) relative to the parent murine antibody. These mutations in the CDRs were made in order to confer optimal specificity and stability on the humanised version of 11B6.

In one embodiment, the antibody polypeptides of the invention bind hK2 with a $K_D$ of greater than $0.1 \times 10^{-9}$ M.

Methods for measuring the overall affinity ($K_D$) and on-rate (ka) and off-rate (kd) of an interaction (such as an interaction between an antibody and a ligand) are well known in the art. Exemplary in vitro methods are described in Example 3 below. It is also conceivable to use flow cytometry based methods (Sklar et al., 2002, *Annu Rev Biophys Biomol Struct*, 31:97-119; the disclosures of which are incorporated herein by reference).

Advantageously, the antibody polypeptide of the invention has an affinity ($K_D$) for hK2 of lower than $1.0 \times 10^{-10}$ M, for example a $K_D$ lower than $9.0 \times 10^{-11}$ M, $8.0 \times 10^{-11}$ M, $7.0 \times 10^{-11}$ M, $6.0 \times 10^{-11}$ M, $5.0 \times 10^{-11}$ M, $4.0 \times 10^{-11}$ M, $3.0 \times 10^{-11}$ M, $2.0 \times 10^{-11}$ M or lower than $1.0 \times 10^{-11}$ M.

It will be appreciated by persons skilled in the art that the antibody polypeptides of the invention may constitute antibody heavy chains, antibody light chains, homodimers and heterodimers of antibody heavy and/or light chains, and antigen binding fragments and derivatives of the same.

In one embodiment, the antibody polypeptide comprises or consists of an intact (i.e. complete) antibody, such as an IgA, IgD, IgE, IgG or IgM molecule.

Advantageously, the antibody polypeptide comprises or consists of an intact IgG molecule, or an antigen-binding fragment or derivative of the same.

The IgG molecule may be of any known subtype, for example IgG1, IgG2, IgG3 or IgG4.

By "antigen-binding fragments and derivatives" of antibodies we include Fv fragments (e.g. single chain Fv and disulphide-bonded Fv), Fab-like fragments (e.g. Fab fragments, Fab' fragments and F(ab)₂ fragments) and domain antibodies (e.g. single $V_H$ variable domains or $V_L$ variable domains).

For example, the antibody polypeptide may comprise or consist of an scFv or Fab fragment.

A further characterising feature of the antibody polypeptides of the present invention is the presence of framework amino acid sequences from one or more human antibodies in the heavy and light chain variable regions.

By "framework sequences" we include the regions of the heavy and light chain variable domains other than the CDRs. Typically, each variable domain will comprise four framework regions, designated FR1 to FR4, within which the CDR sequences are located:

FR1-CDR1-FR2-CDR2-FR3-CDR3-FR4

It will be appreciated that the amino acid sequences of the framework regions may be fully human or may contain one or more backmutations (i.e. the amino acid sequence present in the human framework may be substituted with the amino acid found at the corresponding position within the parent rodent variable domain from which the CDRs are derived). Consequently, the sequences of FR1, FR2, FR3 and/or FR4 of the heavy and/or light chain variable domain(s) of the antibody polypeptide of the invention may be non-naturally occurring.

In one embodiment, the framework sequences of the antibody polypeptide share at least 70% sequence identity with framework regions from one or more human antibodies, for example at least 80%, 85%, 90%, 95%, 96%, 97%, 98%, 99% or more. Thus, the antibody polypeptide may comprise a heavy chain FR1 region that shares least 70% sequence identity with an FR1 region of a human antibody. It will be appreciated, however, that the heavy and light chains of the antibody polypeptide may share sequence identity with the framework regions of different human antibodies.

Percent identity can be determined by, for example, the LALIGN program (Huang and Miller, Adv. Appl. Math. (1991) 12:337-357) at the Expasy facility site (http://www-.ch.embnet.org/software/LALIGN_form.html) using as parameters the global alignment option, scoring matrix BLOSUM62, opening gap penalty −14, extending gap penalty −4. Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (as described in Thompson et al., 1994, *Nucl. Acid Res.* 22:4673-4680, which is incorporated herein by reference). The parameters used may be as follows:

Fast pair-wise alignment parameters: K-tuple(word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

In one embodiment, the framework sequences of the heavy variable domain of the antibody polypeptide of the invention are encoded by the human immunoglobulin VH4 gene family.

For example, the framework sequences may be encoded, at least in part, by a VH4-28 germline gene (e.g. FR1, FR2 and FR3 may be encoded by VH4-28 and FR4 may be encoded by JH1).

Thus, in one embodiment, the antibody polypeptide may comprise or consist of a heavy chain variable region which comprises or consists of the amino acid sequence of SEQ ID NO:8:

[SEQ ID NO: 8]
QVQLQESGPGLVKPSDTLSLTCAVSGNSITSDYAWNWIRQPPGKG

LEWIGYISYSGSTTYNPSLKSRVTMSRDTSKNQFSLKLSSVTAVD

TAVYYCATGYYYGSGFWGQGTLVTVSS

In one embodiment, the framework sequences of the light variable domain of the antibody polypeptide of the invention are encoded by the human immunoglobulin Kappa V4 gene family.

For example, the framework sequences may be encoded, at least in part, by an IgkV4-B3 germline gene (e.g. FR1, FR2 and FR3 may be encoded by IgkV4-B3 and FR4 may be encoded by JK2).

Thus, in one embodiment, the antibody polypeptide may comprise or consist of a light chain variable region which comprises or consists of the amino acid sequence of SEQ ID NO: 9:

[SEQ ID NO: 9]
DIVLTQSPDSLAVSLGERATINCIKASESVEYFGTSLMHWYQQKP

GQPPKLLIYAASNRESGVPDRFSGSGSGTDFTLTISSLQAEDVAV

YYCQQTRKVPYTFGQGTKLEIK

By "at least in part" we include that the framework sequences comprise at least ten contiguous amino acids encoded by the reference gene, for example at least 20 contiguous amino acids. We also include that one or more, but not all, the FR regions are encoded by the reference gene (for example, FR1 and FR2 may be encoded by the reference gene, but not FR3).

In a preferred embodiment, the antibody polypeptide comprises a heavy chain variable region which comprises or consists of the amino acid sequence of SEQ ID NO:8 and a light chain variable region which comprises or consists of the amino acid sequence of SEQ ID NO: 9.

Optionally, the antibody polypeptide of the invention further comprises a heavy chain constant region, or part thereof.

In one embodiment, the antibody polypeptide comprises a CH1, CH2 and/or CH3 region of an IgG heavy chain (such as an IgG1, IgG2, IgG3 or IgG4 heavy chain). Thus, the antibody polypeptide may comprise part or all of the constant regions from an IgG1 heavy chain. For example, the antibody polypeptide may be a Fab fragment comprising CH1 and CL constant regions.

In one embodiment, the antibody polypeptide may comprise an antibody Fc-region. It will be appreciated by a skilled person that the Fc portion may be from an IgG antibody, or from a different class of antibody (such as IgM, IgA, IgD or IgE). In one embodiment, the Fc region is from an IgG1, IgG2, IgG3 or IgG4 antibody.

The Fc region may be naturally-occurring (e.g. part of an endogenously produced antibody) or may be artificial (e.g. comprising one or more point mutations relative to a naturally-occurring Fc region and/or modifications to the carbohydrate moieties within the CH2 domain). Fc-regions with point mutations improving their ability to bind FcR may be advantageous, e.g. by altering serum half life or by modulating (i.e. enhancing or reducing) binding to Fcγ receptors (FcγR) involved in ADCC and CDC.

Advantageously, the antibody polypeptide may comprise the amino acid sequence of SEQ ID NO: 10, or part thereof:

[SEQ ID NO: 10]
A S T K G P S V F P L A P S S K S T S G G T

A A L G C L V K D Y F P E P V T V S W N S G

A L T S G V H T F P A V L Q S S G L Y S L S

S V V T V P S S S L G T Q T Y I C N V N H K

P S N T K V D K K V E P K S C D K T H T C P

P C P A P E L L G G P S V F L F P P K P K D

T L M I S R T P E V T C V V V D V S H E D P

E V K F N W Y V D G V E V H N A K T K P R E

E Q Y N S T Y R V V S V L T V L H Q D W L N

G K E Y K C K V S N K A L P A P I E K T I S

K A K G Q P R E P Q V Y T L P P S R E E M T

K N Q V S L T C L V K G F Y P S D I A V E W

E S N G Q P E N N Y K T T P P V L D S D G S

F F L Y S K L T V D K S R W Q Q G N V F S C

S V M H E A L H N H Y T Q K S L S L S P G K

Optionally, the antibody polypeptide of the invention further comprises a light chain constant region, or part thereof.

In one embodiment, the antibody polypeptide comprises a CL region of an IgG light chain (such as a kappa or lambda light chain)

For example, the antibody polypeptide may comprise the amino acid sequence of SEQ ID NO: 11, or part thereof:

```
                                          [SEQ ID NO: 11]
R T V A A P S V F I F P P S D E Q L K S G T

A S V V C L L N N F Y P R E A K V Q W K V D

N A L Q S G N S Q E S V T E Q D S K D S T Y

S L S S T L T L S K A D Y E K H K V Y A C E

V T H Q G L S S P V T K S F N R G E C
```

Advantageously, the antibody polypeptide comprises a heavy chain constant region which comprises or consists of the amino acid sequence of SEQ ID NO: 10 and a light chain constant region which comprises or consists of the amino acid sequence of SEQ ID NO: 11.

In one preferred embodiment, the antibody polypeptide of the invention comprises:

(a) a heavy chain which comprises or consists of the amino acid sequence of SEQ ID NO: 12 (wherein the variable region is in bold and the CDR sequences are in boxed italics)

```
                                          [SEQ ID NO: 12]
Q V Q L Q E S G P G L V K P S D T L S

L T C A V S G N S I T [S D Y A W N] W I

R Q P P G K G L E W I G [Y I S Y S G S]

[T T Y N P S L K S] R V T M S R D T S K

N Q F S L K L S S V T A V D T A V Y Y

C A T [G Y Y Y G S G F] W G Q G T L V T

V S S A S T K G P S V F P L A P S S K

S T S G G T A A L G C L V K D Y F P E

P V T V S W N S G A L T S G V H T F P

A V L Q S S G L Y S L S S V V T V P S

S S L G T Q T Y I C N V N H K P S N T

K V D K K V E P K S C D K T H T C P P

C P A P E L L G G P S V F L F P P K P

K D T L M I S R T P E V T C V V V D V

S H E D P E V K F N W Y V D G V E V H

N A K T K P R E E Q Y N S T Y R V V S

V L T V L H Q D W L N G K E Y K C K V

S N K A L P A P I E K T I S K A K G Q

P R E P Q V Y T L P P S R E E M T K N

Q V S L T C L V K G F Y P S D I A V E

W E S N G Q P E N N Y K T T P P V L D

S D G S F F L Y S K L T V D K S R W Q
```

-continued
```
Q G N V F S C S V M H E A L H N H Y T

Q K S L S L S P G K
``` and/or (b) a light chain which comprises or consists of the amino acid sequence of SEQ ID NO: 13 (wherein the variable region is in bold and the CDR sequences are in boxed italics)

```
                                          [SEQ ID NO: 13]
D I V L T Q S P D S L A V S L G E R A

T I N C [K A S E S V E Y F G T S L M H]

W Y Q Q K P G Q P P K L L I Y [A A S N]

[R E S] G V P D R F S G S G S G T D F T

L T I S S L Q A E D V A V Y Y C [Q Q T]

[R K V P Y T] F G Q G T K L E I K R T V

A A P S V F I F P P S D E Q L K S G T

A S V V C L L N N F Y P R E A K V Q W

K V D N A L Q S G N S Q E S V T E Q D

S K D S T Y S L S S T L T L S K A D Y

E K H K V Y A C E V T H Q G L S S P V

T K S F N R G E C
```

For example, the antibody polypeptide may comprise or consist of two heavy chains of SEQ ID NO: 12 and two light chains of SEQ ID NO: 13, joined together by disulphide bridges to form a typical IgG antibody structure.

The antibody polypeptides of the invention may comprise or consist of one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. The term 'peptidomimetic' refers to a compound that mimics the conformation and desirable features of a particular peptide as a therapeutic agent.

For example, the said polypeptide includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, which is incorporated herein by reference. This approach involves making pseudo-peptides containing changes involving the backbone, and not the orientation of side chains. Retro-inverse peptides, which contain NH—CO bonds instead of CO—NH peptide bonds, are much more resistant to proteolysis. Alternatively, the said polypeptide may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the said polypeptide may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

It will be appreciated by persons skilled in the art that the antibody polypeptides of the invention may be augmented with a functional moiety to facilitate their intended use, for example as an in vivo imaging agent or therapeutic agent.

Thus, in one embodiment, the antibody polypeptide is linked, directly or indirectly, to a therapeutic moiety.

Any suitable therapeutic moiety may be used. A suitable therapeutic moiety is one that is capable of reducing or inhibiting the growth, or in particular killing, a prostatic cancer cell. For example, the therapeutic agent may be a cytotoxic moiety. A cytotoxic moiety may comprise or consist of one or more radioisotopes. For example, the one or more radioisotopes may each be independently selected from the group consisting of beta-emitters, Auger-emitters, conversion electron-emitters, alpha-emitters, and low photon energy-emitters. It may be desired that the one or more radioisotopes each independently has an emission pattern of locally absorbed energy that creates a high absorbed dose in the vicinity of the agent. Exemplary radioisotopes may include long-range beta-emitters, such as $^{90}$Y, $^{32}$P, $^{186}$Re/$^{188}$Re; $^{166}$Ho, $^{76}$As/$^{77}$As, $^{89}$Sr, $^{153}$Sm; medium range beta-emitters, such as $^{131}$I, $^{177}$Lu, $^{67}$Cu, $^{161}$Tb, $^{105}$Rh; low-energy beta-emitters, such as $^{45}$Ca or $^{35}$S; conversion or Auger-emitters, such as $^{51}$Cr, $^{67}$Ga, $^{99}$Tc$^m$, $^{111}$In, $^{114m}$In, $^{123}$I, $^{125}$I $^{201}$Tl, and alpha-emitters, such as $^{212}$Bi, $^{213}$Bi, $^{223}$Ac, $^{225}$Ac, $^{212}$Pb, $^{255}$Fm, $^{223}$Ra, $^{149}$Tb and $^{221}$At. Other radionuclides are available and will be possible to use for therapy.

In another embodiment, it may be desired that the therapeutic moiety or cytotoxic moiety is not a moiety as disclosed as a "tracer" in WO 2006/087374 A1, in particular at page 11, lines 7-15 thereof.

In one preferred embodiment, the antibody polypeptide is linked to (or otherwise labelled with) the radioisotope $^{177}$Lu.

Alternatively, the therapeutic moiety may comprise or consist of one or more therapeutic (such as cytotoxic) drugs, for example, a cytostatic drug; an anti-androgen drug; cortisone and derivatives thereof; a phosphonate; a testosterone-5-α-reductase inhibitor; a boron addend; a cytokine; thapsigargin and its metabolites; a toxin (such as saporin or calicheamicin); a chemotherapeutic agent (such as an anti-metabolite); or any other therapeutic or cytotoxic drug useful in the treatment of prostatic carcinoma.

Exemplary therapeutic/cytotoxic drugs may, for example, include:

Cytostatics, in particular those with dose-limiting side-effects, including but not limited to cyclophosamide, chlorambucil, ifosfamide, busulphane, lomustine, taxanes, estramustine phosphate and other nitrogen mustards, antibiotics (including doxorubicine, calicheamicines and esperamicine), vinca alkaloids, azaridines, platinum-containing compounds, endostatin, alkyl sulfonates, nitrosoureas, triazenes, folic acid analoges, pyrimidine analoges, purine analogs, enzymes, substituted urea, methyl-hydrazine derivatives, daunorubicin, amphipathic amines, Anti-androgens such as flutamide and bikalutamide and metabolites thereof;

Cortisone and derivatives thereof;

Phosphonates such as diphophonate and buphosphonate;

Testosterone-5-α-reductase inhibitors;

Boron addends;

Cytokines;

Thapsigargin and its metabolites;

Other agents used in the treatment of prostatic carcinoma.

Alternatively, the cytotoxic moiety may comprise or consist of one or more moieties suitable for use in activation therapy, such as photon activation therapy, neutron activation therapy, neutron induced Auger electron therapy, synchrotron irradiation therapy or low energy X-ray photon activation therapy.

For example, with the antibody polypeptides of the invention there will be the potential of using synchrotron radiation (or low energy X-rays) for the advancement of radiotherapy, primarily focusing on so called photo-activation radiotherapy (PAT), in which the local energy deposition from external X-ray irradiation is enhanced in the cancer tissue by the interaction with a pre-administered, high-Z tumor-targeting agent.

The PAT treatment modality utilises monochromatic X-rays from a synchrotron source, such as provided by the ID17 biomedical beamline at the European Synchrotron Radiation Facility (ESRF) in Grenoble, and as anticipated to be available at other facilities in the future such as the new Swedish synchrotron facility, Max-IV.

As a further potential treatment modality, research on "induced Auger electron tumour therapy" is the coming European Spallation Source (ESS) in Lund, and hopefully a medical experimental station. Reactor-produced thermal and semi-thermal neutrons have for long been used for Boron-Neutron-Capture-Therapy, BNCT, both for pre-clinical experiments and for treatment of brain tumours with the induced alpha-particles and the recoil nucleus ($^7$L) that give a high locally absorbed energy. A similar approach is to use neutrons and suitable tumour-targeting molecules labelled with stable nuclei with high cross-section for neutrons. Antibodies or peptides can for instance be labelled with stable Gadolinium ($^{157}$Gd) and act as the target molecule for the neutrons that are captured by the Gd-nucleus, so called Gadolinium Neutron Capture Therapy (GdNCT). By Monte Carlo techniques, the dose distribution in the tumour and the surrounding tissues is calculated as it results from γ-photons, neutrons, nuclear recoils, as well as characteristic x-rays, internal conversion and Auger-electrons from gadolinium or other potential elements.

As discussed above, the therapeutic moiety (such as a radioisotope, cytotoxic moiety or the like) may be linked directly, or indirectly, to the binding moiety (such as an antibody or fragment thereof). Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraaza-cyclododecane-1,4,7,10,tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tet-raacetic acid (TETA), derivatives of 3,6,9,15-Tetraazabicy-clo[9.3.1]-pentadeca-1(15), 11,13-triene-4-(S)-(4-isothio-cyanatobenzyl)-3,6,9-triacetic acid (PCTA), derivatives of 5-S-(4-Aminobenzyl)-1-oxa-4,7,10-triazacyclododecane-4, 7,10-tris(acetic acid) (DO3A) and other chelating moieties. The use of such linkers may be particularly appropriate in circumstances wherein the agent comprises or consists of an antibody or fragment thereof as the binding moiety linked, via a linker, to a radioisotope as the therapeutic moiety.

One preferred linker is DTPA, for example as used in $^{177}$Lu-DTPA-[antibody polypeptide of the invention].

A further preferred linker is deferoxamine, DFO, for example as used in $^{89}$Zr-DFO-[antibody polypeptide of the invention].

Optionally, the antibody polypeptide of the invention may (or may not) further comprises a detectable moiety. For example, a detectable moiety may comprise or consist of a radioisotope, such as a radioisotope selected from the group consisting of $^{99m}$Tc, $^{111}$In, $^{67}$Ga, $^{68}$Ga, $^{72}$As, $^{89}$Zr, $^{123}$I and $^{201}$Tl Optionally, the agent may comprise a pair of detectable and cytotoxic radionuclides, such as $^{86}$Y/$^{90}$Y or $^{124}$I/$^{211}$At. Alternatively, the agent may comprise a radioisotope that is capable of simultaneously acting in a multi-modal manner as a detectable moiety and also as a cytotoxic moiety to provide so-called "Multimodality theragnostics". The binding moieties may thus be coupled to nanoparticles that have the capability of multi-imaging (for example, SPECT, PET, MRI, Optical, or Ultrasound) together with therapeutic capability using cytotoxic drugs, such as radionuclides or chemotherapy agents. Also included with the present invention is the possibility of treatment by hyperthermia using high frequency alternating magnetic fields and accompanied ultrasound imaging.

Alternatively, the detectable moiety may comprise or consist of a paramagnetic isotope, such as a paramagnetic isotope is selected from the group consisting of $^{157}$Gd, $^{55}$Mn, $^{162}$Dy, $^{52}$Cr and $^{56}$Fe.

In the case that the antibody polypeptide comprises a detectable moiety, then the detectable moiety may be detectable by an imaging technique such as SPECT, PET, MRI, optical or ultrasound imaging.

Therapeutic and detectable moieties may be conjugated or otherwise combined with the antibody polypeptide using methods well known in the art (for example, the existing immunoconjugate therapy, gemtuzumab ozogamicin [trade-name: Mylotarg®], comprises a monoclonal antibody linked to the cytotoxin calicheamicin).

In a further embodiment, the antibody polypeptide of the invention is used to treat prostate cancer in the form of a formulation comprising a population of antibody polypeptide molecules. In one option, all (or substantially all, such as greater than 90%, 95%, 99%, 99.9% or more, by weight) of the antibody polypeptide molecules in the population comprise the same therapeutic moiety. In another option, the population comprises a mixture of other agents with different therapeutic moieties. This option will give possibilities to enhance the effects of targeted radionuclide therapy using various agents such chemotherapy agents, hormonal therapy agents or other combination of therapies in which the targeting agent not only delivers therapeutically active radionuclides to tumor associated antigens but also simultaneously radiosensitizes the targeted tumor cells by modulating (e.g. triggering or blocking) an intracellular signaling cascade. This option is also useful in treating the prostate cancer with a mixture of cytotoxic agents, for example, using a cocktail of alpha- and different ranges of beta-emitters, or a cocktail of radionuclides with different range, LET (linear energy transfer) and RBE (relative biological effect), for combined treatment of large tumors, micrometastases, and single tumor cells. In one embodiment, long-range emitters may be used for treatment of large tumors, and short-range emitters may be used for the treatment of smaller tumours such as micrometastases, and single tumor cells.

Optionally, the antibody polypeptide of the present invention may (or may not) further comprises a moiety for increasing the in vivo half-life of the agent. Exemplary moieties for increasing the in vivo half-life of the agent may include polyethylene glycol (PEG), human serum albumin, glycosylation groups, fatty acids and dextran. PEG may be particularly contemplated.

It will be appreciated that the polypeptides of the invention may be lyophilised for storage and reconstituted in a suitable carrier prior to use, e.g. through freeze drying, spray drying, spray cooling, or through use of particle formation (precipitation) from supercritical carbon dioxide. Any suitable lyophilisation method (e.g. freeze-drying, spray drying, cake drying) and/or reconstitution techniques can be employed. It will be appreciated by those skilled in the art that lyophilisation and reconstitution can lead to varying degrees of activity loss and that use levels may have to be adjusted upward to compensate. Preferably, the lyophilised (freeze dried) polypeptide loses no more than about 1% of its activity (prior to lyophilisation) when rehydrated, or no more than about 5%, 10%, 20%, 25%, 30%, 35%, 40%, 45%, or no more than about 50% of its activity (prior to lyophilisation) when rehydrated.

Methods for the production of polypeptides of the invention are well known in the art.

Conveniently, the polypeptide is or comprises a recombinant polypeptide. Suitable methods for the production of such recombinant polypeptides are well known in the art, such as expression in prokaryotic or eukaryotic hosts cells (for example, see Sambrook & Russell, 2000, *Molecular Cloning, A Laboratory Manual*, Third Edition, Cold Spring Harbor, N.Y., the relevant disclosures in which document are hereby incorporated by reference).

Antibody polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that polypeptides of the invention may alternatively be synthesised artificially, for example using well known liquid-phase or solid phase synthesis techniques (such as t-Boc or Fmoc solid-phase peptide synthesis).

A second aspect of the invention provides an isolated nucleic acid molecule encoding an antibody polypeptide of the invention, or a component polypeptide chain thereof. By "nucleic acid molecule" we include DNA (e.g. genomic DNA or complementary DNA) and mRNA molecules, which may be single- or double-stranded.

In one embodiment, the nucleic acid molecule is a cDNA molecule.

It will be appreciated by persons skilled in the art that the nucleic acid molecule may be codon-optimised for expression of the antibody polypeptide in a particular host cell, e.g. for expression in human cells (for example, see Angov, 2011, *Biotechnol. J.* 6(6):650-659).

In a preferred embodiment, the nucleic acid molecule of the invention comprises
(a) the nucleotide sequence of SEQ ID NO: 14

```
                                            [SEQ ID NO: 14]
CAG GTT CAG CTG CAG GAA AGC GGA CCT GGC TTG

GTG AAA CCC AGC GAT ACC CTT AGC CTG ACA TGT

GCT GTG TCT GGC AAT TCC ATC ACT TCC GAC TAT

GCG TGG AAC TGG ATT CGG CAA CCA CCG GGA AAA

GGG CTC GAG TGG ATA GGG TAC ATC AGC TAT TCT

GGT TCA ACC ACG TAC AAT CCC TCA CTG AAG AGT

AGG GTT ACC ATG TCC AGA GAC ACC TCC AAG AAC

CAG TTC AGC CTG AAG CTG AGT AGT GTG ACA GCC

GTA GAT ACA GCC GTC TAT TAC TGC GCA ACA GGG

TAC TAC TAT GGC TCT GGC TTT TGG GGT CAA GGA

ACT CTC GTC ACT GTG TCA AGC
``` and/or
(b) the nucleotide sequence of SEQ ID NO: 15

```
                                            [SEQ ID NO: 15]
GAC ATA GTG CTC ACT CAG AGC CCT GAT AGC TTG

GCT GTC AGT CTT GGG GAA AGA GCC ACC ATC AAC

TGC AAA GCG TCC GAA AGC GTC GAG TAT TTC GGG

ACT AGC CTG ATG CAC TGG TAT CAG CAG AAA CCC

GGA CAA CCG CCT AAG CTG CTG ATC TAT GCA GCC

TCT AAT CGC GAA AGT GGC GTT CCA GAC AGG TTT

TCC GGT TCT GGA TCA GGC ACA GAC TTC ACC CTC

ACG ATT TCC TCA CTG CAA GCT GAG GAT GTA GCC

GTG TAC TAC TGT CAG CAG ACA CGG AAA GTG CCC

TAC ACC TTT GGT CAG GGC ACA AAG CTG GAG ATT

AAG
```

Also included within the scope of the invention are the following:
(a) a third aspect of the invention provides a vector (such as an expression vector) comprising a nucleic acid molecule according to the second aspect of the invention;
(b) a fourth aspect of the invention provides a host cell (such as a mammalian cell, e.g. human cell) comprising a nucleic acid molecule according to the second aspect of the invention or a vector according to the third aspect of the invention; and
(c) a fifth aspect of the invention provides a method of making an antibody polypeptide according to the first aspect of the invention comprising culturing a population of host cells according to the fourth aspect of the invention under conditions in which said polypeptide is expressed, and isolating the polypeptide therefrom.

A sixth aspect of the invention provides a pharmaceutical composition comprising a pharmaceutically effective amount of an antibody polypeptide of the first aspect of the invention and a pharmaceutically-acceptable diluent, carrier or excipient.

Additional compounds may also be included in the pharmaceutical compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g., through freeze drying, spray drying, spray cooling, or through use of particle formation from supercritical particle formation.

By "pharmaceutically acceptable" we mean a non-toxic material that does not decrease the effectiveness of the kallikrein protein-binding activity of the agent of the invention. Such pharmaceutically acceptable buffers, carriers or excipients are well-known in the art (see *Remington's Pharmaceutical Sciences*, 18th edition, A. R Gennaro, Ed., Mack Publishing Company (1990) and *Handbook of Pharmaceutical Excipients*, 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the agent in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the agent of the invention. The adjuvant may be one or more of zinc, copper or silver salts with different anions, for example, but not limited to fluoride, chloride, bromide, iodide, thiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The antibody polypeptides of the invention may be formulated into any type of pharmaceutical composition known in the art to be suitable for the delivery thereof.

In one embodiment, the pharmaceutical compositions of the invention may be in the form of a liposome, in which the antibody polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the antibody polypeptides may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active antibody polypeptide. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, and rectal. Also administration from implants is possible. Infusion may be a desired route because of the potentially high cytotoxicity of the administered agent.

In one embodiment, the pharmaceutical compositions are administered parenterally, for example, intravenously, intracerebroventricularly, intraarticularly, intra-arterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (for example, to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g., intravenous administration or local administration to a tumour in a patient (for example, intra-tumourally or peri-tumourally).

The pharmaceutical compositions will be administered to a patient in a pharmaceutically effective dose, i.e. a therapeutically effective absorbed dose of the therapeutic radionuclide.

In the context of therapeutic use of the antibody polypeptides of the invention, a 'pharmaceutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e., a carrier or administration vehicle. Further, it is intended to mean an amount sufficient to reduce and/or prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical worker based on patient characteristics, such as age, weight, sex, condition, complications, other diseases, etc., as is well known in the art (see Example 8 below). The administration of the pharmaceutically effective dose can be carried out both by single administration in the form of an individual dose unit or else several smaller dose units and also by multiple administrations of subdivided doses at specific intervals. Alternatively, the does may be provided as a continuous infusion over a prolonged period.

In the context of diagnostic use of the antibody polypeptides of the invention, a 'pharmaceutically effective amount', or 'effective amount', or 'diagnostically effective', as used herein, refers to that amount which provides a detectable signal for in vivo imaging purposes.

The antibody polypeptides of the invention can be formulated at various concentrations, depending on the efficacy/toxicity of the compound being used. The formulation may comprises the polypeptide at a concentration of between 0.1 µM and 1 mM, between 1 µM and 500 µM, between 500 µM and 1 mM, between 300 µM and 700 µM, between 1 µM and 100 µM, between 100 µM and 200 µM, between 200 µM and 300 µM, between 300 µM and 400 µM, between 400 µM and 500 µM and about 500 µM.

Typically, the therapeutic dose of the antibody polypeptide (with or without a therapeutic moiety) in a human patient will be in the range of 100 µg to 700 mg per administration (based on a body weight of 70 kg). For example, the maximum therapeutic dose may be in the range of 0.1 to 10 mg/kg per administration, e.g. between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

It will be appreciated by persons skilled in the art that the pharmaceutical compositions of the invention may be administered alone or in combination with other therapeutic agents used in the treatment of a prostate cancer, or before, after or at the same time as the treatment of the patient with other therapeutic modalities for the treatment of prostate cancer, such as other therapeutic antibodies, surgery (e.g., radical prostatectomy), radionuclide therapy, brachytherapy, external beam radiation therapy, high-intensity focused ultrasound (HIFU), chemotherapy, oral chemotherapeutic drugs, cryosurgery (freezing the tumour), hormonal therapy (such as antiandrogen therapy), castration or combinations of the foregoing.

A seventh aspect of the invention provides a kit comprising an antibody polypeptide according to the first aspect of the invention or a pharmaceutical composition according to the sixth aspect of the invention, together with instructions for use of the same as described herein.

An eighth aspect of the invention provides an antibody polypeptide according to the first aspect of the invention for use in medicine.

A ninth aspect of the invention provides an antibody polypeptide according to the first aspect of the invention for use in the treatment and/or diagnosis of prostate cancer.

A tenth aspect of the invention provides a method of treatment of prostate cancer in a subject, the method comprising administering to the subject a therapeutically effective amount of a antibody polypeptide according to the first aspect of the invention.

By 'treatment' we include both therapeutic and prophylactic treatment of the patient. The term 'prophylactic' is used to encompass the use of an agent, or formulation thereof, as described herein which either prevents or reduces the likelihood of prostate cancer, or the spread, dissemination, or metastasis of localised prostate cancer in a patient or subject. The term 'prophylactic' also encompasses the use of an agent, or formulation thereof, as described herein to prevent recurrence of prostate cancer in a patient who has previously been treated for prostate cancer.

An eleventh aspect of the invention provides a method of diagnosis of prostate cancer in a subject, the method comprising administering to the subject a diagnostically effective amount of a antibody polypeptide according to the first aspect of the invention.

By "diagnosis" we include the detection of prostate cancer cells, either in vivo (i.e. within the body of a patient) or ex vivo (i.e. within a tissue or cell sample removed from the body of a patient).

The prostate cancer to be treated or diagnosed may be localised to the prostate, or may be a non-localised (that is, disseminated) prostate cancer. Prostate cancer localised to the prostate may, for example, be classified as clinical T1 or T2 cancers according to the TNM system (abbreviated from Tumor/Nodes/Metastases) whereas non-localised/disseminated prostate cancer may, for example, be classified as clinical T3 or T4 cancers.

The prostate cancer to be treated or diagnosed may be a metastatic prostate cancer. Metastasis refers to the spread of a cancer from its original location to other sites in the body. For example, the metastatic prostate cancer to be treated or diagnosed may be a metastases present in the lymphatic system; in bone (including spine, vertebrae, pelvis, ribs); metastasis within pelvis, rectum, bladder, or urethra. Metastases present at other less common locations can also be treated with the present invention. The metastases may be micrometastases. Micrometastase is a form of metastases in which the newly formed tumors are generally too small to be detected, or detected with difficulty. For example, the present invention provides the skilled person with means to treat single cancer cells or cell clusters, even if the presence of such cells or clusters are not possible to diagnose but exist, for example as occult disseminated disease.

Accordingly, it is anticipated that a particularly important technical advantage of the treatment provided by the present invention compared to the prior art treatments of prostate cancer is the enhanced efficacy in treatment of disseminated and/or metastatic (including micrometastatic) prostate cancer.

Thus, in one embodiment, the invention provides antibody polypeptides and methods for preventing or treatment metastasis of a primary prostate tumour.

Prostate cancer tends to develop in men over the age of fifty, more commonly in men over 60, 65 or 70, and although it is one of the most prevalent types of cancer in men, many never have symptoms, undergo no therapy, and eventually die of other causes. This is because cancer of the prostate is, in most cases, slow-growing, symptom-free, and since men with the condition are older they often die of causes unrelated to the prostate cancer, such as heart/circulatory disease, pneumonia, other unconnected cancers, or old age. About two-thirds of prostate cancer cases are slow growing, the other third more aggressive and fast developing.

Accordingly, the development of effective methods for the treatment and diagnosis of prostate cancer is particularly important for management of more aggressive and fast developing forms of the cancer, particularly in younger patient. Accordingly, in one embodiment, the invention relates to the treatment or diagnosis of prostate cancer in a patient who is less than 90, 85, 80, 75, 70, 65, 60, 55, 50, 45, 40 or less years old at the time of diagnosis of prostate cancer and/or at the time of treatment.

Men who have a first-degree relative (father or brother) with prostate cancer are thought to have twice the risk of developing prostate cancer, and those with two first-degree relatives affected are thought to have a five-fold greater risk compared with men with no family history. Accordingly, the invention may relate to the treatment or diagnose of prostate cancer in a patient that is characterised in that one, two, or more, family members, in particular first-degree family members (such as a father or brother), has been previously been diagnosed with prostate cancer.

The invention also relates to the treatment or diagnosis of prostate cancer in a patient, wherein the prostate cancer to be treated has castration-resistant prostate cancer (CRPC). CRPC may be characterised by typically becoming refractory to hormone treatment after one to three years, and resuming growth despite hormone therapy.

In the medical uses and methods of the invention, the antibody polypeptide is typically injected or infused into the body of the patient. In vivo, the antibody polypeptide then binds to tissues that produce the target antigen, hK2; primarily, prostate cancer cells and metastases thereof. Upon binding, the antibody polypeptide may directly exert a therapeutic effect (e.g. inducing cell death via ADCC, CDC or by virtue of carrying a radioisotope or other cytotoxic moiety). Alternatively, the bound antibody polypeptide may serve as a diagnostic (imaging) tool, which may guide the choice of therapy or aid surgical removal of the cancer cells.

It will be appreciated by persons skilled in the art that the antibody polypeptides of the invention may be used in combination with other therapeutic and/or diagnostic agents/treatment, such as external radiotherapy, surgery, cytostatic and androgen treatments.

The foregoing description focuses on embodiments of the present invention applicable to methods for the treatment and diagnosis of prostatic cancer. However, it will be appreciated that the invention is not limited to such applications but may be useful for post-operative examinations, and examinations during or after radiation, cytostatic, and androgen treatments.

In another embodiment RadioGuided Surgery (RGS) or Image-Guided Surgery (IGS) may be used to identify tracer-labeled antibody polypeptides of the invention during and/or before surgery. Thus, an antibody polypeptide comprising a detectable moiety as discussed above may be administered during and/or before surgery. In this embodiment the antibody polypeptides may first be infused. Thereafter, RGS/IGS may be used to identify hK2-producing tissue with a detection instrument sensitive to the detectable moiety, during or before surgery. The detectable moiety may, for example, be a radiation emitting or magnetic-sensitive detectable moiety; it may, for example, be an emitter of Cerenkov radiation and/or Bremsstrahlung; it may be a fluorescent label and/or a magnetic or magnetizable label. Accordingly, the RGS/IGS according to the present invention may, for example, be a method that is based on the detection of optical, Cerenkov, Bremsstrahlung, or beta radiation; the detection of a radionuclide label, and/or may involve magnetometry. RGS is well known to the person skilled in the art as a surgical technique that enables the surgeon to identify tissue "marked" by the detectable moiety.

The visualisations obtained according to the above methods may be combined with other radiological visualisation methods, such as SPECT/PET, computed tomography (CT), ultrasound (US), and magnetic resonance imaging (MRI).

Accordingly, in a further aspect, the present invention also provides antibody polypeptides for use in medicine by administration to a patient with prostate cancer before or during the surgery, such as RadioGuided or Image-Guided Surgery.

A still further aspect of the invention provides an in vitro method for the detection of prostate tumour cells in the blood of a subject, the method comprising:
(a) providing a sample of blood from a subject to be tested;
(b) optionally, extracting and/or purifying cells present in the blood sample;
(c) contacting an antibody polypeptide according to the first aspect of the invention with cells present in the blood sample;
(d) determining (directly or indirectly) whether the antibody polypeptide binds to free (i.e. uncomplexed) hK2 wherein the binding of the antibody polypeptide to free hK2 is indicative of the presence of prostate tumour cells in the blood of a subject.

Thus, the method comprises performing an assay to determine whether the blood sample contains free hK2; the presence of free hK2 being indicative of the presence of prostate tumour cells in the blood of a subject.

Persons skilled in the art will appreciate that there are many ways to perform such an assay. For example, the immunoassay could be either homogeneous or, more preferably, heterogenous. The assay could also performed in either a competitive or, more preferably, a non-competitive format.

In the case of the heterogeneous, non-competitive assay, an exemplary protocol could be:
(a) providing a sample of blood from a subject to be tested;
(b) optionally, extracting and/or purifying cells present in the blood sample;
(c) contacting a solid phase immobilized antibody polypeptide according to the first aspect of the invention with cells present in the blood sample;
(d) washing to remove soluble components (not bound to solid surface);
(e) adding the tracer, i.e. another anti-hK2 specific antibody labelled with a reporter molecule/particle;
(f) washing to remove unbound tracer antibody; and
(g) detecting the signal from the tracer antibody Between steps b & c or c & d, there should typically be an incubation period to allow the cell to produce soluble hK2, then for it to be detected.

An additional aspect of the invention provides an in vitro method for the detection of prostate tumour cells in the tissue of a subject, the method comprising
(a) providing a sample of tissue (such an a histological sample) from a subject to be tested;
(b) optionally, extracting and/or purifying cells present in the tissue sample;

(c) contacting an antibody polypeptide according to the first aspect of the invention with cells present in the tissue sample;

(d) determining (directly or indirectly) whether the antibody polypeptide binds to free (i.e. uncomplexed) hK2 wherein the binding of the antibody polypeptide to free hK2 is indicative of the presence of prostate tumour cells in the tissue of a subject.

In one embodiment of the above in vitro methods, step (d) is performed by ELISA. However, any assay suitable for detecting antibody-antigen interactions in vitro may be used.

In an additional embodiment, the method further comprises quantification of the prostate tumour cells in the sample.

In a further embodiment of the above in vitro methods, the method is for the diagnosis of prostate cancer in a subject.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the above description and the accompanying drawings. It should be understood, however, that the above description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The following drawings form part of the present specification and are included to further demonstrate certain aspects of the present invention. The invention may be better understood by reference to one or more of these drawings in combination with the detailed description of specific embodiments presented herein.

FIG. 1: The sequences of the heavy and light chain variable regions of the exemplary humanised 11B6 Fab fragment of the invention.

Figure 2:
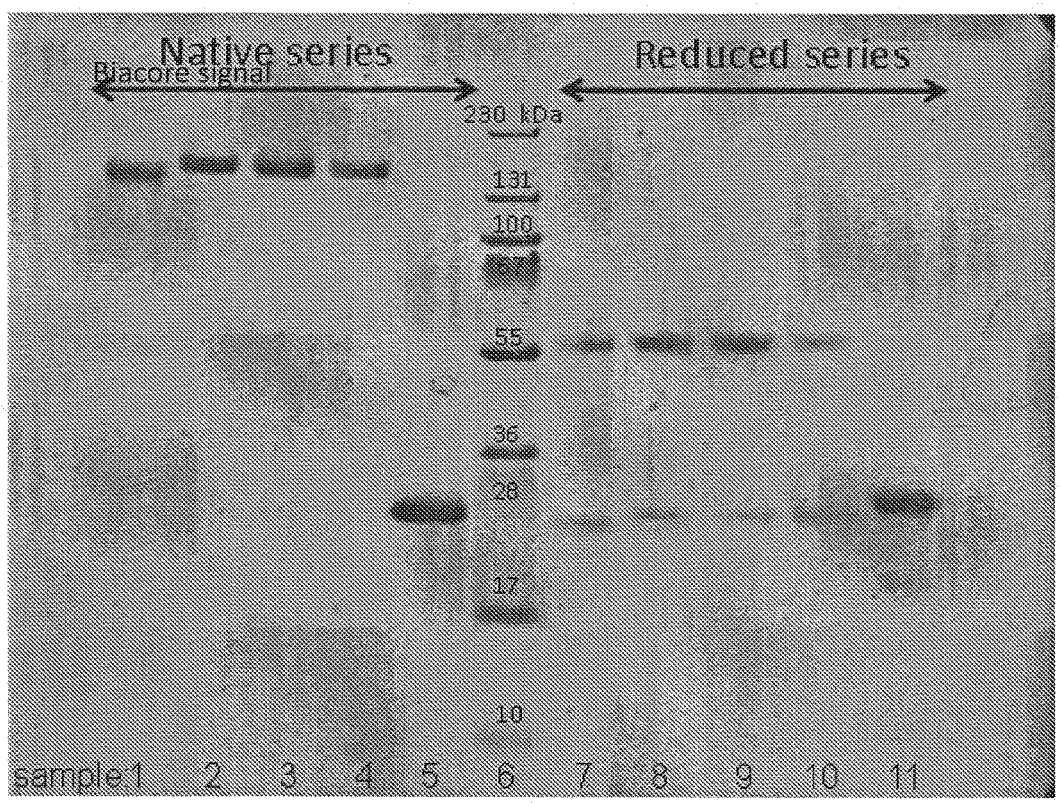

FIG. 2: SDS-PAGE gel with native and reduced samples of murine and humanised 11B6 antibodies.

Figure 3:
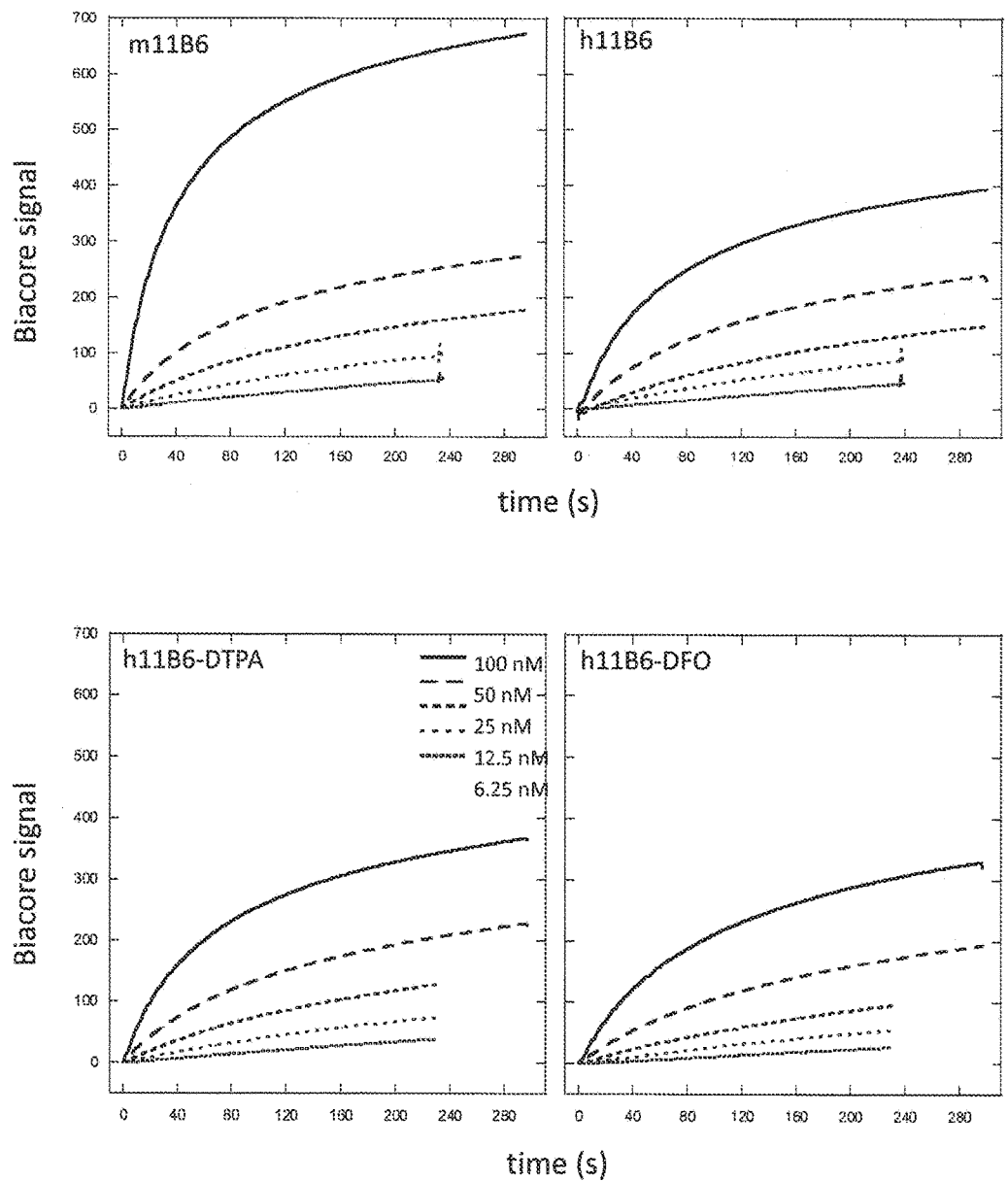

FIG. 3: Association phases upon binding of the test 11B6 antibodies to hK2 on a chip.

Figure 4:
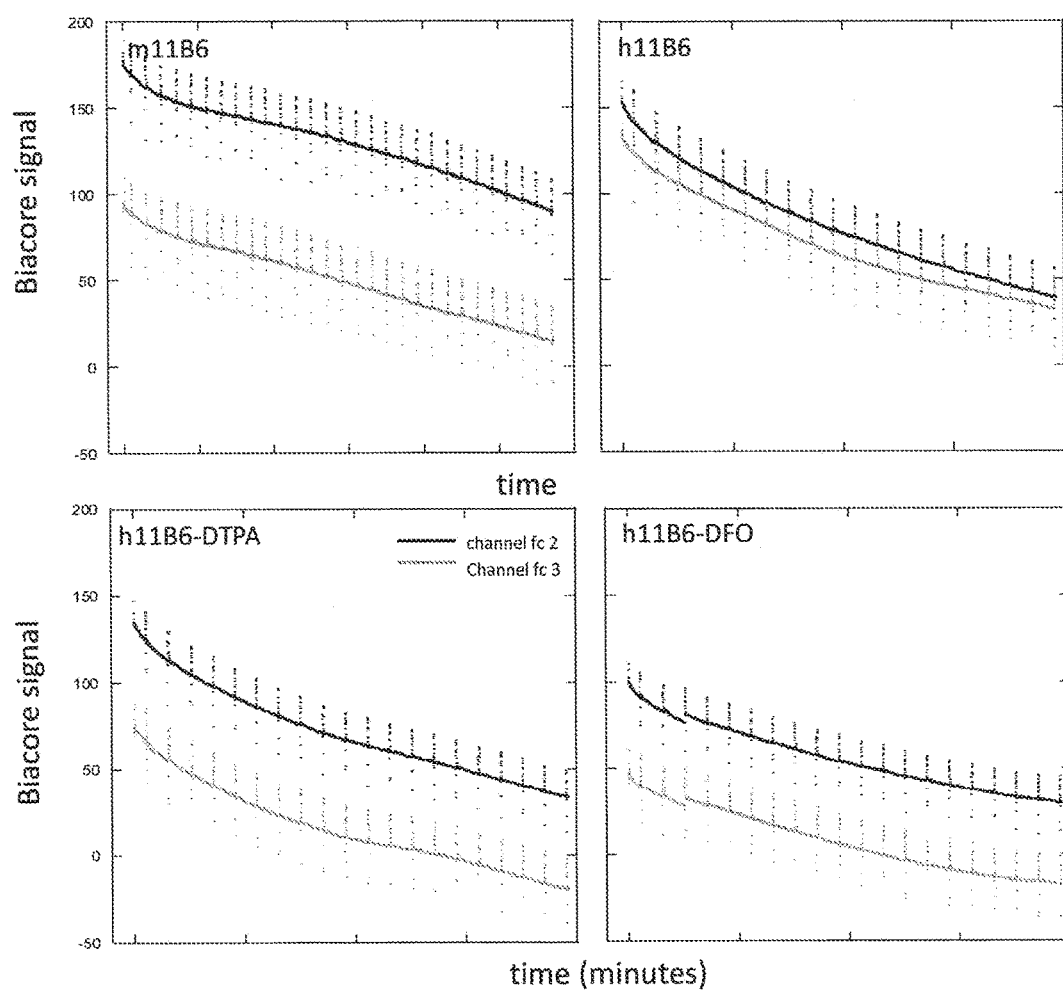

FIG. 4: Dissociation phases of the test 11B6 antibodies.

Figure 5:
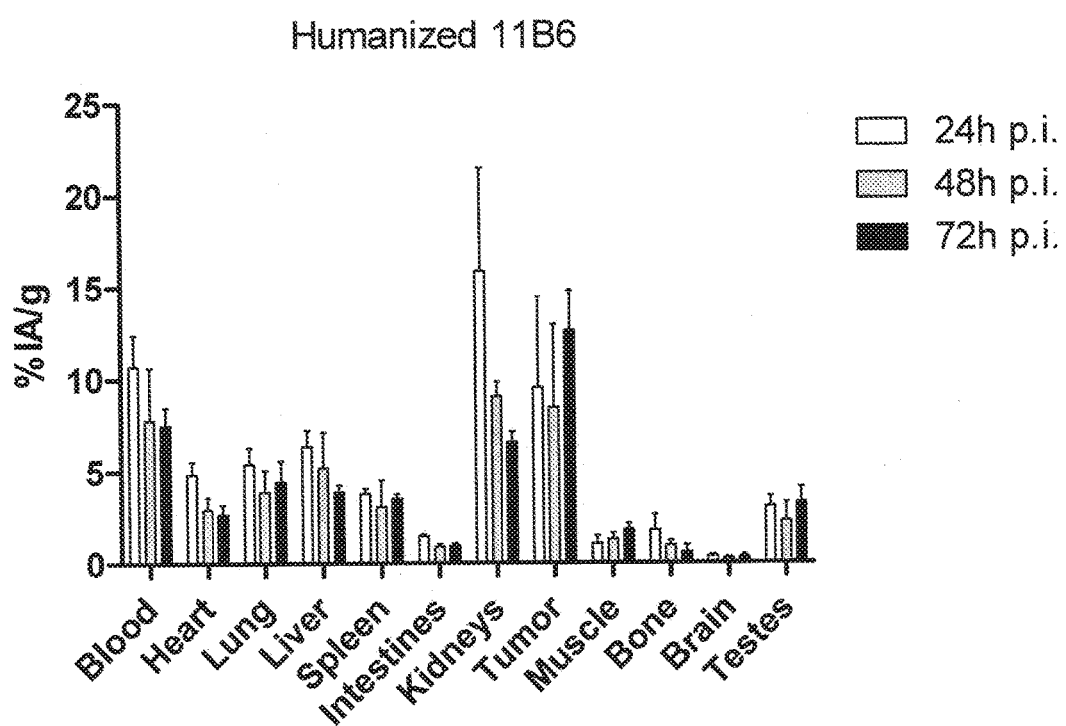

FIG. 5: Biodistribution of $^{177}$Lu-labelled humanised 11B6 antibodies.

Figure 6:
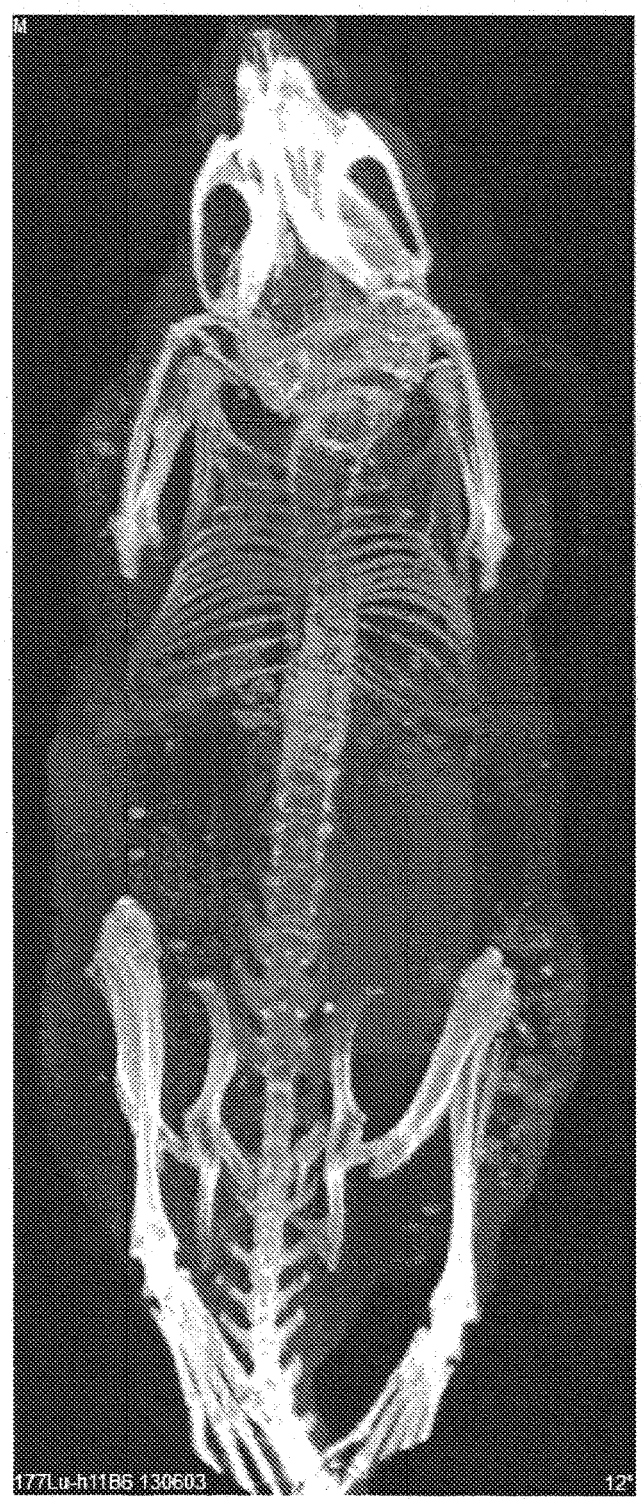

FIG. 6: Exemplary SPECT image showing binding of $^{177}$Lu-labelled h11B6 to prostate tumour in mice.

Figure 7:
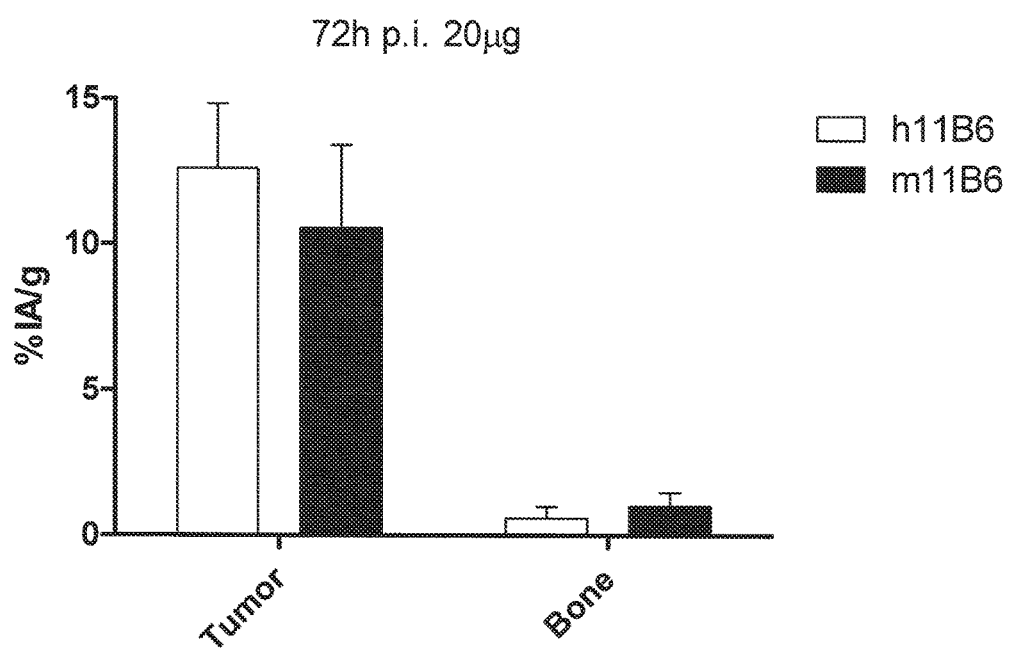

FIG. 7: Percentage uptake of $^{177}$Lu-labelled h11B6 and m11B6 in tumour and bone.

Figure 8:
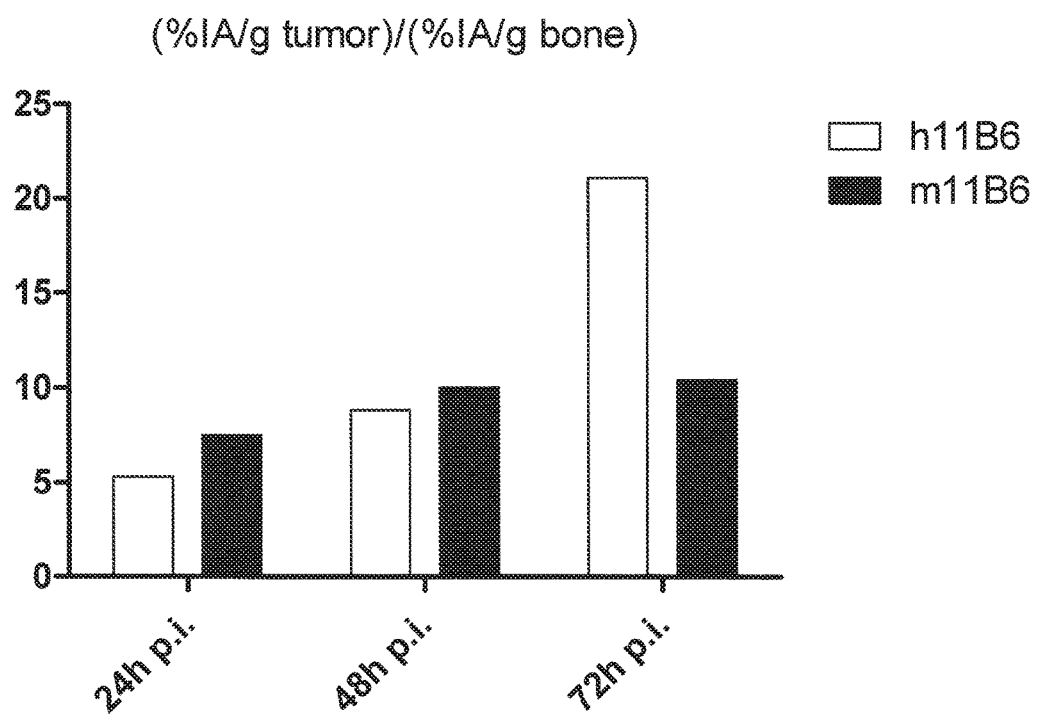

FIG. 8: Ratio of percentage uptake per gram of $^{177}$Lu-labelled h11B6 and m11B6 in tumour to bone.

Figure 9A:
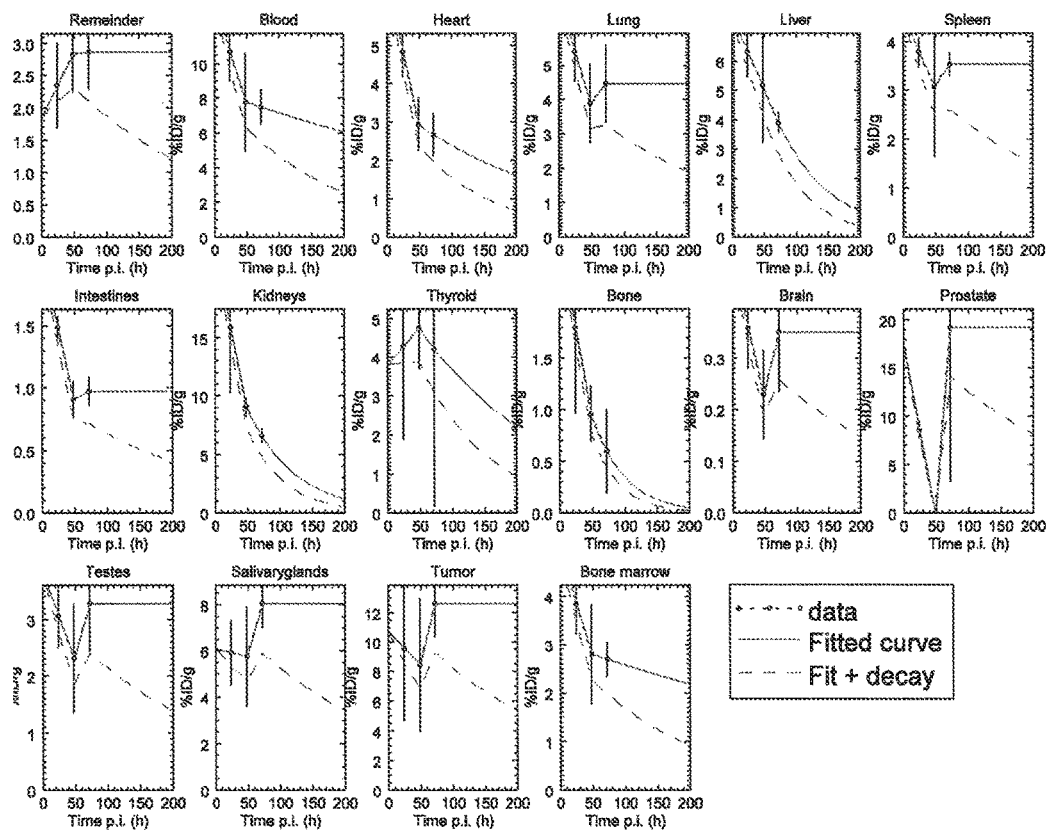
Figure 9B:
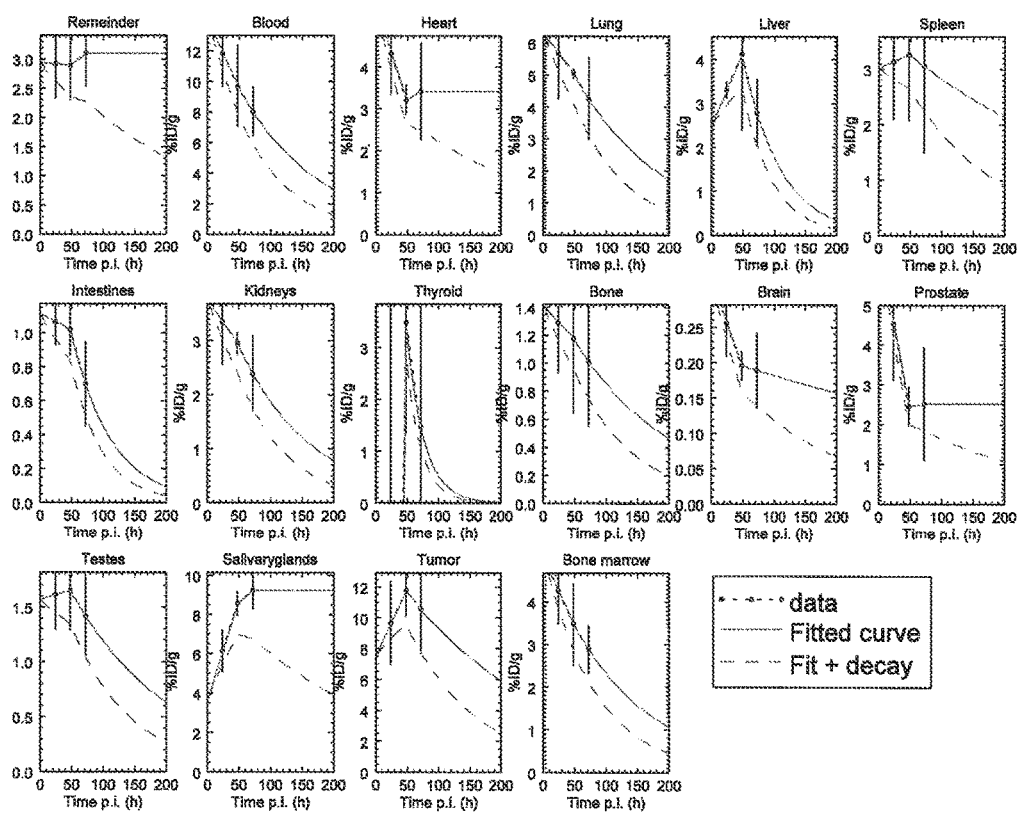

FIG. 9: Kinetics of the (a) humanised 11B6 antibody and (b) murine 11B6 antibody.

Figure 10:
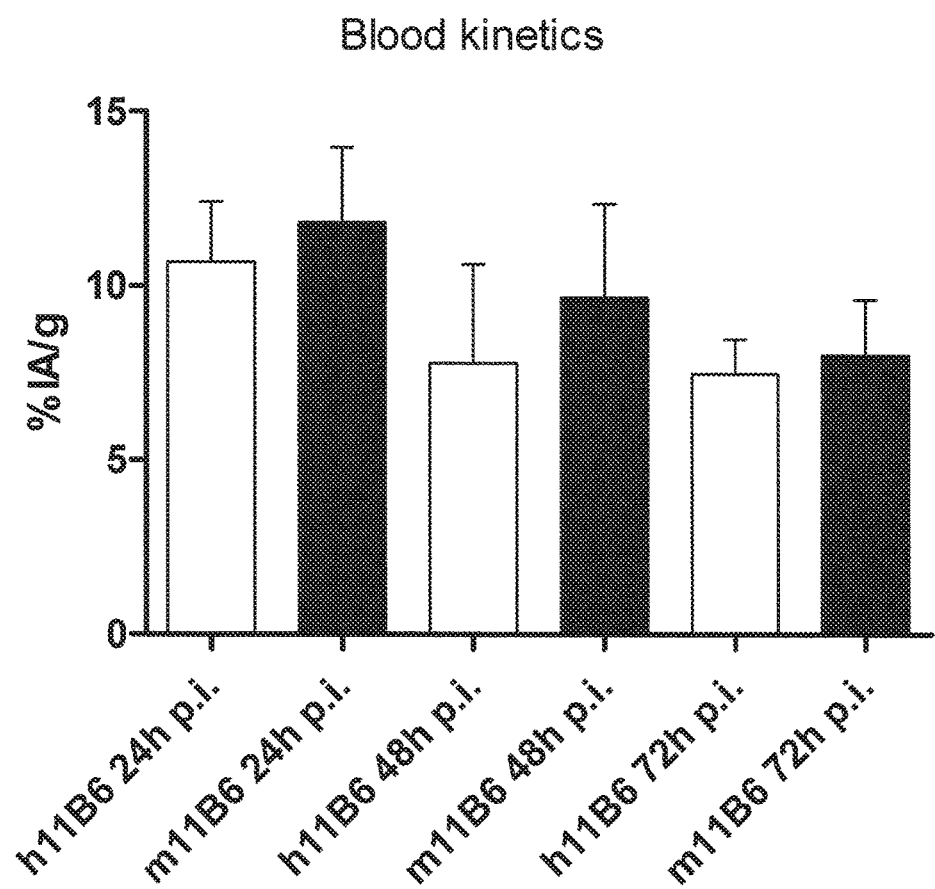

FIG. 10: Clearance of $^{177}$Lu-labelled h11B6 and m11B6 from the blood.

Figure 11:

FIG. 11: Representative photographs of tumour size before (top image) and after (bottom image) treatment with $^{177}$Lu-11B6.

Figure 12A:
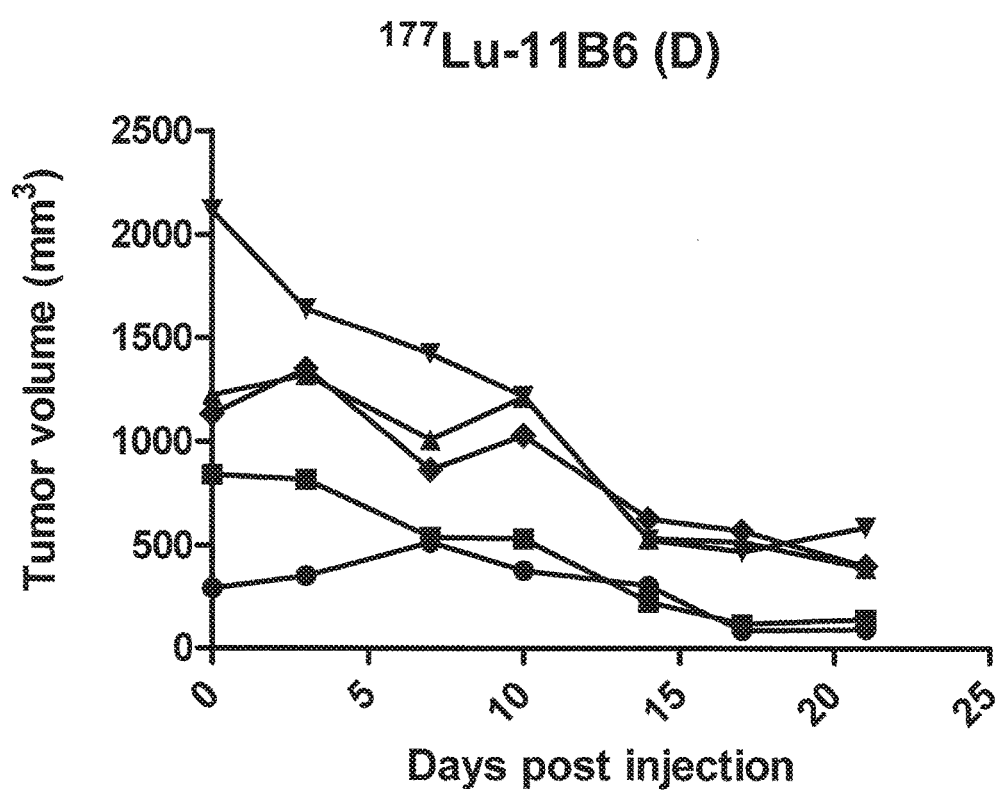
Figure 12B:
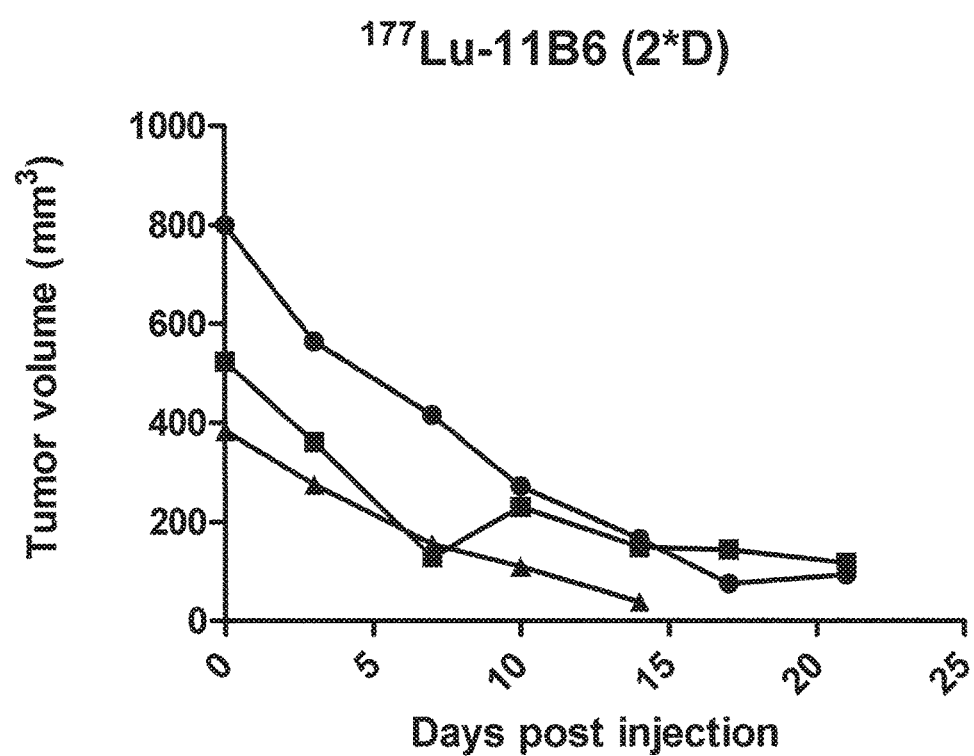
Figure 12C:
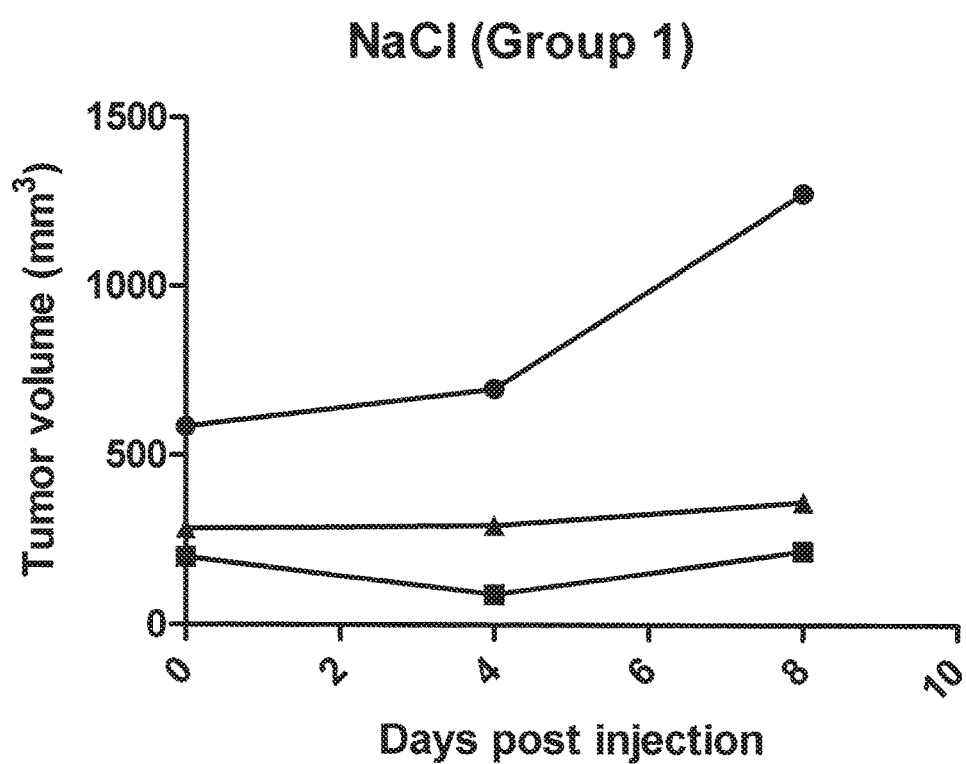

FIG. 12: Summary of the effect of (a) single radioactivity amount 'D' of $^{177}$Lu-11B6, (b) double radioactivity amount '2×D' of $^{177}$Lu-11B6 and (c) control treatment on tumour size in LNCaP xenografts.

Figure 13:
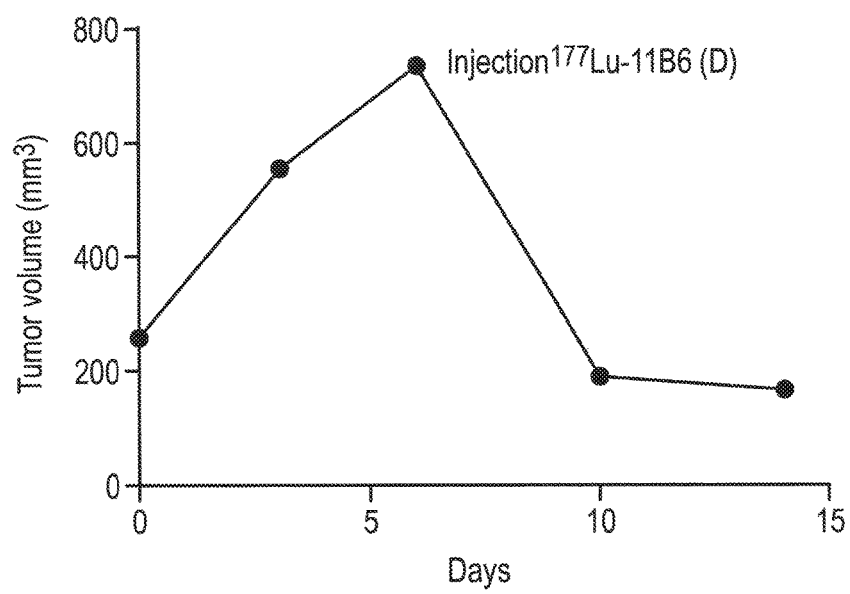
Figure 13:
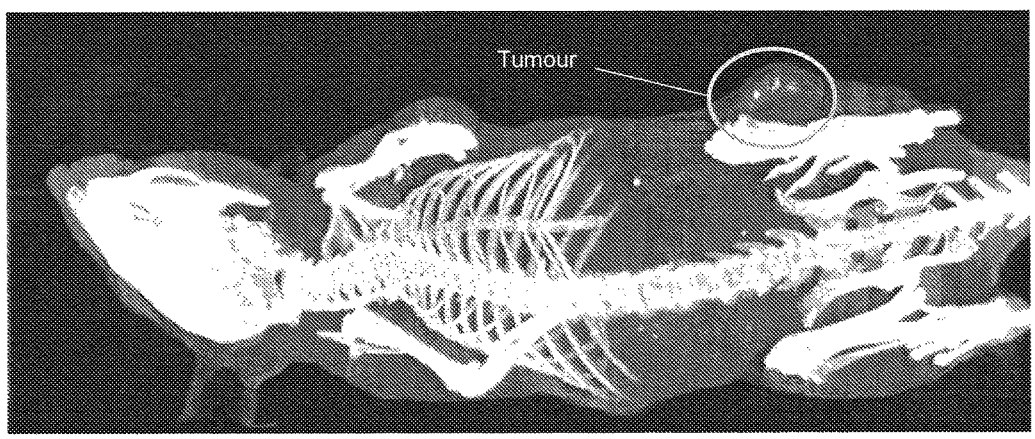

FIG. 13: (a) tumour growth data and (b) a SPECT image for one LNCaP xenografts mouse treated with a single dose $^{177}$Lu-11B6.

FIG. 14: Tumour volume as a function of days post injection for (a) animals receiving $^{177}$Lu-labelled h11B6 antibody according to the invention, (b) animals receiving $^{177}$Lu-labelled non-specific IgG 'isotype control' antibody and (c) animals receiving NaCl only. Treatment was administered on Day 0. Animals were terminated in the event of the following occurrences: large tumour volumes (diameter >14 mm); large weight loss (weight loss >15% compared to initial weight); negatively affected general condition; or a combination of all these three parameters. (numbers to the right are the ID number of each animal)

Figure 14A:
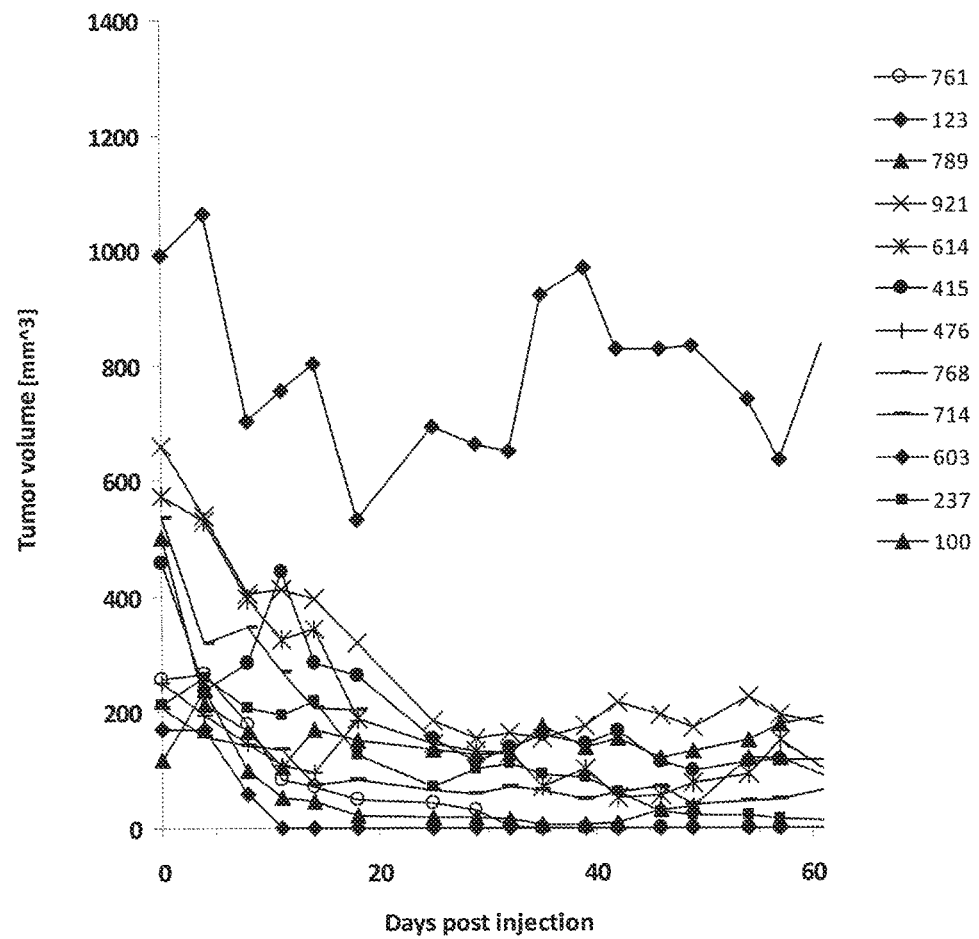
Figure 14B:
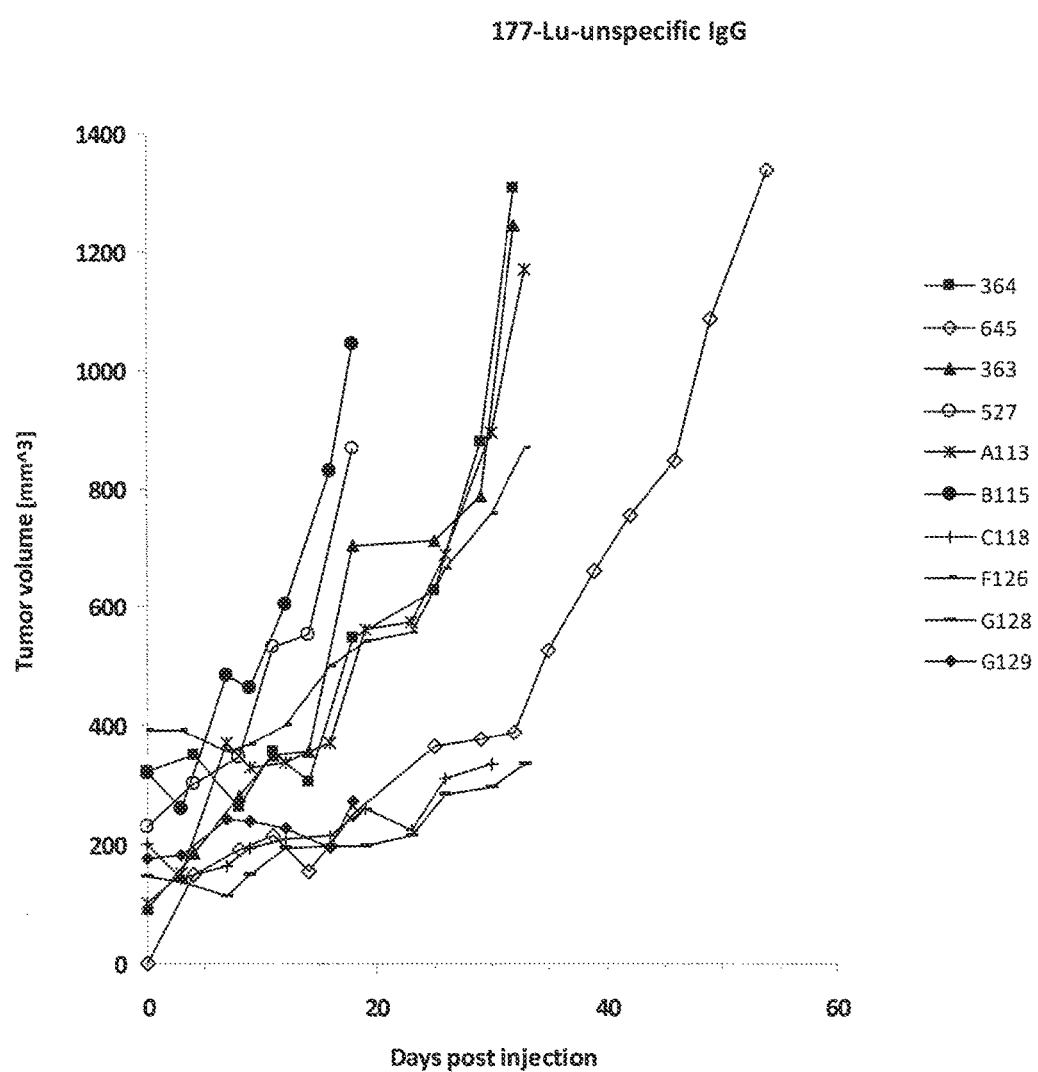
Figure 15:
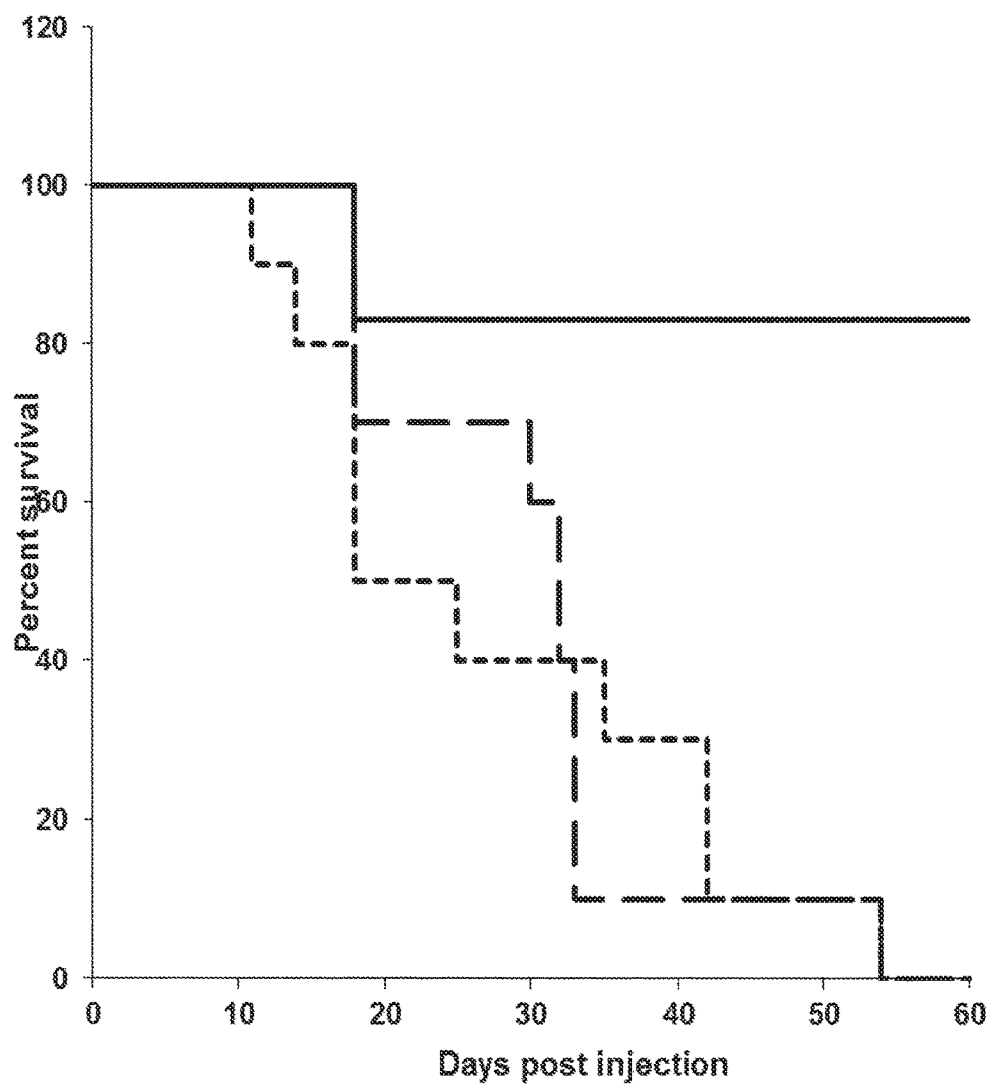

FIG. 15: Kaplan-Meier curve for the three treatment groups shown in FIG. 14. Solid line: $^{177}$Lu-h11B6; broken line: $^{177}$Lu-labelled non-specific IgG Isotype control' antibody; dotted line: NaCl.

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1—Cloning of 11B6 from Hybridoma Cell Line

Reagents

Monoclonal antibody 11B6 producing hybridoma cell line was used for mRNA extraction and production of antibodies which were further affinity purified for protein sequencing (Väisänen et al., 2004).

Restriction enzymes, FastAP and T4 DNA ligase were from Fermentas, primers from the University of Turku, Department of Biotechnology (WO252) and from Thermo Scientific. DNA purifications were done with Qiagen's Gel extraction and PCR purification kits.

mRNA Extraction and cDNA Synthesis mRNA was extracted from 11B6 MAb producing hybridoma cells (5E6 cells) with QuickPrep Micro mRNA purification kit (Amersham Biosciences) and cDNA synthesis from the mRNA was done with Applied Biosystems' High-capacity cDNA archive kit according to instructions.

Amplification of Antibody Genes from cDNA

N-terminal sequences of the purified 11B6 MAb heavy (H) and light (L) chains were determined by Edman degradation at the University of Helsinki protein sequencing service. Light chain sequence was DIVLTQSPAS [SEQ ID NO: 16] and the heavy chain sequence DVQLQESGPG [SEQ ID NO: 17]. IMGT database comparison of amino acids identified the genes: IGKV3 and IGHV3, respectively. The complementary regions for forward PCR primers (degenerate) were designed based on the DNA sequences (found by NCBI BLAST) coding the N-terminal amino acids. Reverse primer used to clone the heavy chain was designed to bind $C_{H1}$. In the case of the light chain, two reverse primers were used; the one used in the first PCR binds to $C_L$ and the other one used in second PCR to the border of $V_L$ and $C_L$. All primers also contain the restriction enzyme recognition sites needed for cloning (later underlined).

Light chain forward primer was SfiI_DIVLTQSPAS [SEQ ID NO: 16]:

```
(5'-TTACTCGCGGCCCAGCCGGCCATGGCGGAYATHGTRYTVA
CNCARTCTCC-3'; [SEQ ID NO: 18])
``` and reverse primers WO252

```
(5'-GCGCCGTCTAGAATTAACACTCATTCCTGTTGAA-3',
XbaI; [SEQ ID NO: 19])
and

CpoI_JK2
(5'-GATACAGTTGGTGCAGCATCGGTCCGTTTTATTTCCAG
CTTGGTCCCCCT-3'; [SEQ ID NO: 20]).
```

Heavy chain forward primer was NotI_DVQLQESGPG [SEQ ID NO: 17]

```
(5'-TGCTGCTGGCGGCCGCTCCAGCCATGGCTGAYGTVCARCT
KCAGGAGTCDGG-3'; [SEQ ID NO: 21])
``` and reverse primer asCH1_SacI

```
(5'-CGCCACCAGAGCTCTCACAATCCCTGGGCACAATTTTC-3';
[SEQ ID NO: 22]).
```

$V_L+C_L$ fragment was amplified in PCR reaction containing 100 ng cDNA as template, 0.2 mM dNTP's, 0.5 μM primers SfiI DIVLTQSPAS [SEQ ID NO: 16] and WO252, 1× Phusion HF buffer and 0.6 U Phusion DNA polymerase (Finnzymes). Amplification was done by protocol of 98° C. 30 sec, 30 cycles of 98° C. 7 sec, 50° C. 20 sec, 72° C. 20 sec, and final extension of 72° C. 10 min. After sequencing the PCR product and finding out the sequence of $V_L$-$C_L$ border the PCR for actual cloning was done again from cDNA in a reaction like above except with primers SfiI_DIVLTQSPAS [SEQ ID NO: 16] and CpoI_JK2 to clone only the $V_L$ part. Amplification was done by protocol of 98° C. 30 sec, 10 cycles of 98° C. 7 sec, 60° C. 20 sec, 72° C. 20 sec, 25 cycles of 98° C. 7 sec, 56° C. 20 sec, 72° C. 20 sec, and final extension of 72° C. 10 min.

$V_H+C_{H1}$ fragment was amplified in a reaction like with $V_L$ except with primers NotI_DVQLQESGPG [SEQ ID NO: 17] and asCH1_SacI. Amplification protocol was 98° C. 30 sec, 30 cycles of 98° C. 7 sec, 64° C. 20 sec, 72° C. 20 sec, and final extension of 72° C. 10 min.

Cloning

The correct sized products were purified from the preparative agarose gel. $V_L$ was digested with SfiI and CpoI, $V_H+C_{H1}$ with SacI and NotI. Recipient vector pAK400 5404 FAb Ich (modified from pAK400, Krebber et al., 1997) was digested separately with both enzyme combinations, fragments dephosphorylated with FastAP and purified from the preparative gel.

Digested 1186 $V_L$ and the corresponding vector fragment were ligated with T4 DNA ligase and transformed by electroporation into *Escherichia coli* XL1-Blue cells (Stratagene) to produce vector pAK400-11B6-VL. Ligation product of SacI+NotI digested $V_H+C_{H1}$ and vector fragment was called pAK400-11B6-VH+CH1. Correct clones were confirmed by DNA sequencing and comparing sequences to the original protein sequences and to the antibodies found on the database (BLAST search).

To construct the complete 11B6 Fab, both previously made constructs were digested with NotI and SacI. Vector pAK400-11B6-VL was used as recipient vector to which $V_H+C_{H1}$ from vector pAK400-11B6-VH+CH1 was inserted. Ligation and transformation were done as above. The constructed pAK400 11B6 FAb Ich vector was confirmed with restriction enzyme analysis.

REFERENCES

Barbas C F 3rd, Kang A S, Lerner R A, Benkovic S J. (1991) Assembly of combinatorial antibody libraries on phage surfaces: The gene III site. Proc. Nat. Acad. Sci., Vol. 88, pp. 7978-7982

Biomagnetic Techniques in Molecular Biology: Technical handbook. Dynal A. S, $2^{nd}$ edition, 1995

Krebber A, Bornhauser S, Burmester J, Honegger A, Wilulda J, Bosshard H R, Plückthun A. (1997) Reliable cloning of functional antibody variable domains from hybridomas and spleen cell repertoires employing a reengineered phage display system. J Immunol Methods. 201(1):35-55

Lilja H, Christensson A, Dahlén U, Matikainen M T, Nilsson O, Pettersson K, Lövgren T. (1991) Prostate-specific antigen in serum occurs predominantly in complex with alpha 1-antichymotrypsin. Clin Chem. 37(9):1618-25

Pajunen M, Saviranta P, Jauria P, Karp M, Pettersson K, Mäntsälä P, Lovgren T. (1997) Cloning, sequencing, expression and characterization of three anti-estradiol-17beta Fab fragments. Biochim Biophys Acta. 1351(1-2): 192-202

Väisänen V, Eriksson S, Ivaska K K, Lilja H, Nurmi M, Pettersson K. (2004) Development of sensitive immunoassays for free and total human glandular kallikrein 2. Clin Chem. 50(9):1607-17

Example 2—Humanisation of the 11B6 Antibody

The variable domain of the murine anti-hK2 antibody 11B6 was humanised using CDR-grafting method. In this approach, the complementarity determining regions (CDR) of the murine antibody were grafted to the variable heavy and light domain frameworks. In addition residues at CDR regions, the residues in the certain critical positions at the framework regions were retained as murine-like rather than turned to human-like in order to maintain the conformation of grafted CDR loops as similar as possible to their conformation in the parental murine antibodies.

Kabat numbering scheme (Kabat et al., 1991) is used throughout this description.

Homology Modelling

An homology model of the murine 11B6 antibody was generated by using automatic Web antibody modelling—Server (VAM; http://antibody.bath.ac.uk/index.html). The model was used for visual inspection based evaluation of the importance of the residues differing in between the parental murine antibodies and the human immunoglobulin sequences used as frameworks for the variable domain humanization, respectively.

Design of the 11B6 Humanised V-Domain Sequences $V_L$ Domain Design

The amino acid sequence of the murine 11B6 light chain variable domain was compared to the database of human immunoglobulin germline sequences in NCBI using ClustalW sequence alignment program. 11B6 $V_L$ was found share the highest similarity with the human germline gene B3 (IGKV4-1*01), the only member of the human $V_{K4}$ family.

Concerning the J-segment encoding the C-terminal part of the variable domain sequence, the human $J_{κ2}$ was found to be the most similar with the corresponding region of the murine 11B6.

The human B3 gene together with sequence of IGKJ2 were used as a framework for the grafting of the CDR-loops (FIG. 1) from the light chain of parental murine antibody 11B6. Residue of murine origin (leucine) was introduced in the position 4 of $V_L$ instead of human-like methionine. This Vernier zone (Foote and Winter, 1992) residue is located directly underneath CDR1 and CDR3 loops of light chain. At the position 54 in CDR-L2 human-like arginine was used instead of murine-like valine. According to modelling, the residue at this position is unlikely form direct interaction with the antigen, however, Arg54 seems to form a salt bridge with the negatively charged aspartate at the position 60 in the human framework. It was considered unlikely that the residue at the position 24 in CDR-L1 is involved in antigen contacting. Consequently, human-like lysine was introduced in this position instead of murine-like arginine.

$V_H$ Domain Design

The amino acid sequence of the murine 11B6 heavy chain variable domain was compared to the database of human immunoglobulin germline sequences in NCBI using clustalW sequence alignment program. 11B6 $V_H$ was found have the highest similarity with the human $V_{H4}$ family member VH4-28. Concerning J-segment encoding the C-terminal part of the variable domain sequence, the human $J_{H1}$ was found to be the most similar with the corresponding region of the murine 11B6.

The human $V_{H4}$-28 gene together with sequence of $J_{H1}$ were used as a framework for the grafting of the CDR-loops (FIG. 1) from the heavy chain of the parental murine antibody 11B6.

Murine-like residues asparagine and threonine were introduced at the positions 27 and 30 of $V_H$, respectively. Although not belonging to CDR-H1 according to the Kabat definition (Kabat et al., 1991; FIG. 1), they are classified as CDR residues by some other CDR definition procedures such as that by Chothia (1989). Residues 27 and 30 can affect the structure of the other parts of the CDR-H1 and possibly participate in direct contacts with the antigen. The residue at the position 71 is known the play important role in maintaining the conformation of the CDR-H2 (Tramontano et al., 1990), and murine-like arginine was used here instead of human-like valine. At the position 94 preceding the important CDR-H3 loop, the murine 11B6 derived residue threonine was introduced instead of human VH4-28 like arginine. In addition, it was considered unlikely that the residue at the position 60 in CDR-H2 is involved in antigen contacting. Therefore, human-like asparagine was introduced at this position instead of murine-like serine.

The genes encoding the humanized 11B6 as Fab fragment, where the designed $V_H$ and $V_L$ domains were joined to the human $C_{H1}$ and human $C_κ$ constant domains, respectively, were purchased as a synthetic construct (Genscript, US). The genes were cloned into the expression vector pAK400Fab modified from pAK400 (Krebber et al., 1997) using SfiI restriction enzyme having recognition sites on the either side of the Fab cassette. The vector was transformed into *E. coli* XL-1 blue cells for the expression of the humanised Fab fragment.

The sequences of the heavy and light chain variable regions of the exemplary humanised 11B6 Fab fragment of the invention are shown in FIG. 1.

REFERENCES

Chothia, C., Lesk, A. M., Tramontano, A., Levitt, M., Smith-Gill, S. J., Air, G., Sheriff, S., Padlan, E. A., Davies, D., Tulip, W. R., Colman, P. M., Spinelli, S., Alzari, P. M., and Poljak, R. J. (1989) Conformations of immunoglobulin hypervariable regions Nature, 342, 877-883

Kabat, E. A., Wu, T. T., Perry, H. M., Gottesman, K. S and Foeller, C. (1991) Sequences of Immunological Interest, 5$^{th}$ edit., NIH, Bethesda, Md.

Krebber A, Bornhauser S, Burmester J, Honegger A, Wilduda J, Bosshard H R, Plückthun A. (1997) Reliable cloning of functional antibody variable domains from hybridomas and spleen cell repertoires employing a reengineered phage display system. J Immunol Methods. 201(1):35-55

Tramontano, A., Chothia, C. and Lesk, A. M. (1990) Framework Residue 71 is a Major Determinant of the Position and Conformation of the Second Hypervariable Region in the $V_H$ Domains of Immunoglobulins. J. Mol. Biol. 215, 175-182

Example 3—Expression and Purification of h11B6

HEK293 cells were expanded in to a 2 L suspension culture in FreeStyle 293 Expression Medium (Life Technologies). The cell density was on the day for transfection 1×10$^6$ cells/ml.

The nucleotide sequences encoding the component heavy or light chains (i.e. SEQ ID NOs: 14 and 15, respectively) were codon-optimized for expression in mammalian cells, synthesized and cloned to IgG expression vectors. The plasmid DNA (expression vector) containing the nucleotide sequences for the heavy and light chains was then mixed with the transfection agent and incubated for 10 min in RT. The DNA-transfection agent-mix was slowly added to cell culture while slowly swirling the flask. The transfected cell culture was then incubated at 37° C., 8% $CO_2$ on an orbital shaker platform rotating at approx. 135 rpm, for seven days.

Culture medium was harvest by centrifugation and filtered through 5 μm, 0.6 μm and 0.22 μm filter systems.

Antibodies were purified by Protein G chromatography and the buffer was changed to PBS pH 7.4 by dialysis; subsequently, the antibodies were concentrated by ultrafiltration.

Concentration was measured by absorbance.

DNA: Light chain: p11B6VLhV1 hk (4300 bp) amount: 0.35 mg

Heavy chain: p11B6VHhV1 hIgG1 (4900 bp) amount: 0.6 mg

The DNA amounts were not optimized.

Transfection agent: proprietary (however, suitable commercially-available transfection agents are readily available, such as Xfect™ Transfection Reagent (Clontech), Lipofectamine (Life Technologies), FuGENE® HD Transfection Reagent (Promega), FreeStyle™ Max Reagent (Invitrogen), DEAE-dextran, polyethylenimine and calcium phosphate).

Overall yield: 13.1 mg (~6.5 mg/L)

Example 4—Characterisation of h11B6: Affinity

Aims of Study

The aim of the study was to investigate the binding kinetics between four variants of the antibody 11B6 and the antigen hK2 by using the technique of Surface Plasmon Resonance (SPR) on a Biacore instrument.

In order to investigate the quality of the protein samples (antibodies and antigen), a SDS-PAGE gel was run prior to the SPR experiments.

In a Pre-Study, different parameters were investigated in order to find the appropriate conditions for the experiments in the Study.

In the Study, multiple binding measurements were performed for the four antibodies and the antigen. From the collected data, the association and dissociation rate constants ($k_{on}$ and $k_{off}$) and the dissociation constants (KD) were calculated and reported here.

Reagents and Instrument Information

Following solutions of the four antibodies and one antigen were provided by Diaprost AB:

m11B6 stock: a-ehk211B6 14.12013 PP, 3.41 mg/ml: 0.9% NaCl, 100 μl h11B6 stock: Innovagen Lot 90476.30 2013 Apr. 12, 1 mg/ml: PBS pH 7.4, 320 μl h11B6-DTPA stock: 0.2M Na-acetate pH 5.5, 0.9 mg/ml, 340 μl h11B6-DFO stock: 5 mg/ml gentisin acid in 0.2M ammonium acetate pH 5.5, 1.6 mg/ml, 400 μl hK2 stock: 26.6 μg/ml frakt 2 fr 7 SL+protein inh 5/2-02 1% BSA All the samples were aliquoted and kept in −20° C. freezer prior to analysis.

All binding experiments were performed on CM4 chip on a Biacore 3000 instrument. The chip and all the reagents needed for activation, immobilization, deactivation, binding and regeneration were purchased from GE Healthcare and used according to the guidelines from the manufacturer.

SDS-Page (a) Description of the Experiment

The reagents provided by Diaprost AB were run on a TRIS-Tricine 10-20% acrylamide gel from Novex according to the guidelines from the manufacturer.

Two series of the protein samples, native and reduced, were run simultaneously on the same gel together with a standard sample.

Each sample in the native series contained: 1-1.3 μg of the protein, TRIS-buffer pH 8.8, SDS and loading buffer.

Each sample in the reduced series contained: 1-1.3 μg of the protein, TRIS-buffer pH 8.8, SDS, loading buffer and 0.04% v/v beta2-merkaptoethanol (the reducing agent).

The staining of the gel was performed in commasie brilliant blue solution of acetic acid, ethanol and water with the corresponding proportions of 0.7, 3.0, 6.3.

The destaining of the gel was performed in the solution of acetic acid, ethanol and water with the corresponding proportions of 0.7, 3.0, 6.3.

(b) Results & Conclusions

The results are shown in FIG. 2.

It is evident from these results that the antibody and antigen samples are of high quality and purity.

Affinity Study (a) Immobilisation of Antigen on a CM4 Chip

Activation of the chip CM4-2 was performed according to manufacturer's guidelines for amine coupling using EDC and NHS mixture.

A solution containing 2.96 μg/ml of the antigen hK2 (stock solution of hK2 diluted in 10 mM NaAc-buffet pH 3.8) was flown over channels fc2-4 on the chip CM4-2 in order to immobilize the antigen to the chip. Flow rate: 5 μl/min, volume: 200 μl.

Target RU ≤ Mw/10   Mw(hk2) = 25 900 Da   Target RU (hk2) ≤ 2590

Channel fc1 was used as a blank.
The following immobilization was achieved:

| fc2 = 1104 RU | fc3 = 731 RU | fc4 = 688 RU |

All channels (fc1-4) were blocked by ethanolamine after activation and immobilization.

These data demonstrate that appropriate immobilization was achieved using 2.96 μg/ml of the antigen.

(b) Investigation of the Association Phase

The association phase of the four antibodies to the chip CM4-2 was followed for 4-5 minutes when solutions of 5 different concentrations of each antibody (stock solutions diluted in HSP-buffer) were flown over the channels fc2-4 on the chip CM4-2 with a rate of 30 μl/min.

The investigated concentrations for each antibody were: 100, 50, 25, 12.5 and 6.25 nM.

Additionally association data was obtained from the experiments where the dissociation process was followed for 480 minutes.

In total, 18 individual association experiments for each antibody were performed.

The signal from the blank, fc1, was subtracted for all the data.

In FIG. 3, the association phases in channel fc2 on chip CM-2 for each of the antibodies at the 5 different concentrations are shown.

We found that after 4-5 minutes, we were able to fit the data for the association processes.

(c) Investigation of the Dissociation Phase

The dissociation phase was followed for 480 minutes for each of the antibodies after flowing a solution of 50 nM of the antibody for 5 minutes over the channels fc2-4 on the chip CM4-2 with a rate of 30 μl/min (FIG. 4).

The signal from the blank, fc1, is subtracted in all the data used in the calculations of the dissociation rate constant.

The data indicate that the dissociation processes are very slow. For all four antibodies, the signal in channel fc4 was drifting and the dissociation process could not be followed in that channel.

(d) Estimation of the Dissociation Rate Constant ($k_{off}$)

The dissociation phase data was fitted and the dissociation rate constants (koff) were estimated (see Table 2).

TABLE 2

| Antibody | $K_{off}(10^{-5}s^{-1})$fc2 | $K_{off}(10^{-5}s^{-1})$fc3 | $K_{off}(10^{-5}s^{-1})$fc4 | Mean | Std dev |
|---|---|---|---|---|---|
| m11B6 | 1.9 | 4.9 | — | 3.4 | ±2.1 |
| h11B6 | 6.4 | 6.9 | — | 6.7 | ±0.4 |
| h11B6-DTPA | 6.3 | 19.1 | — | 12.7 | ±9.1 |
| h11B6-DFO | 5.8 | 5.5 | — | 5.7 | ±0.2 |

Based on the two measurements taken for each antibody, there appears to be no significant difference between the dissociation rate constants ($k_{off}$) of the tested antibodies.

(e) Estimation of the Association Rate Constant ($k_{on}$)

In order to estimate the association rate constants, the dissociation rate constants (Table 2) were used in the fitted equations.

All fitted data was used in order to calculate an average value of the association rate constant and the standard deviation for each antibody (see Table 3).

TABLE 3

| Antibody | No. of expts fitted | Mean $k_{on}$ ($10^5 M^{-1}s^{-1}$) | Std dev |
|---|---|---|---|
| m11B6 | 18/18 | 2.48 | ±0.85 |
| h11B6 | 15/18 | 1.17 | ±0.38 |
| h11B6-DTPA | 17/18 | 1.82 | ±0.54 |
| h11B6-DFO | 18/18 | 1.11 | ±0.22 |

Based on the 15-18 measurements taken for each antibody, there appears to be no significant difference between the association rate constants ($k_{on}$) of the tested antibodies.
(f) Estimation of the Dissociation Constant ($k_D$)

Dissociation constant ($K_D$) for each of the tested antibodies are shown in Table 4.

TABLE 4

| Antibody | Mean $K_D$ $10^{-11}$ M | Std dev |
|---|---|---|
| m11B6 | 19 | ±15 |
| h11B6 | 65 | ±25 |
| h11B6-DTPA | 93 | ±78 |
| h11B6-DFO | 54 | ±13 |

The dissociation constants ($K_D$) are in the $10^{-12}$ M range for all four antibodies.

Although not statistically significant, the dissociation constant for the humanised antibody appears to be higher than that of the parent murine antibody.

Conjugation of the humanised antibody does not appear to affect the affinity noticeably since the $K_D$ is not significantly changed for h11B6-DTPA or h11B6-DFO.

Summary
- The association processes are very fast for all four antibodies and the association rate constants ($k_{on}$) are all in the $10^5$ M$^{-1}$ s$^{-1}$ range based on 15-18 experiments for each antibody.
- The dissociation processes are very slow and almost in the range of technical limitations of Biacore. The dissociation rate constants ($k_{off}$) are all in the $10^{-5}$ s$^{-1}$ range based on two experiments for each antibody.
- The dissociation constants ($K_D$) are in the $10^{-12}$ M range for all four antibodies.

Example 5—Characterisation of h11B6: Aggregation

Executive Summary

Dynamic light scattering (DLS) studies have been carried out on 4 variants of the IgG in order to study their propensity to aggregate. The DLS results show that all constructs have a reasonable size (200 kDa or slightly above 200 kDa assuming a spherical protein) and little or no aggregation.

Objective

To characterise four IgG constructs with respect to oligomeric state using dynamic light scattering. Insulin was used as a control.

Results

Dynamic Light Scattering

Phosphate buffered saline (PBS pH 7.4) was filtrated through 0.22 micron filter. The delivered protein was diluted to 0.1 mg/ml in PBS pH 7.4. Dynamic light scattering was measured at 20° C. in duplicate samples using the Malvern APS equipment. Each sample was measured three times. The dilution buffer was used as control to make sure that the buffer was reasonably free from dust and aggregates, FIG. 1c. All samples could be reliably measured using the number distribution function. The average radius of the most abundant species was calculated along with the polydispersity of the species. The average mass distribution of this species was also calculated, see table 5.

TABLE 5

Dynamic light scattering data derived from size distribution

| Construct | Average radius (nm) | Polydispersity (%) | Mass distribution (%) |
|---|---|---|---|
| Insulin | 2.8 | 28 | 100 |
| h11B6 | 5.7 | 15 | 99.2 |
| M11B6 | 5.7 | 17 | 100 |
| DFO-h11B6 | 6.0 | 22 | 99.9 |
| H11B6-DTPA | 6.1 | 22 | 100 |

Polydispersity = Standard deviation of radius/Average radius × 100%

The insulin control (4 mg/ml 20 mM Na2HPO4, 10 mM Na3EDTA) have an average radius of 2.8 nm which is about 37 kDa. In solution insulin is known to form hexamers of about 35 kDa. A radius of 5.7 nm corresponds to a molecular weight of about 200 kDa for a protein having a perfect spherical shape. A radius of 6.1 nm corresponds to a molecular weight of about 230 kDa for a protein having a perfect spherical shape. This is reasonably close to the molecular weight of 150 kDa for IgG molecules, which means that most of the samples primarily consist of monomeric and/or dimeric IgG molecules. The reason for not excluding dimers is that light scattering give a rough size estimate based on molecular shape and this makes it difficult to separate monomers and dimers but easy to separate large aggregates from monomers or monomers from hexamers (as in the insulin case).

Conclusions

Dynamic light scattering shows that all constructs have a reasonable size and little or no aggregation. The size distributions for all four constructs are overlapping (data not shown).

Example 6—Characterisation of h11B6: In Vivo Biodistribution

This study compares biodistribution in vivo of murine 11B6 and human 11B6 when labeled to $^{177}$Lu.

Material and Methods

Materials $^{177}$Lu was purchased from Mallinkrodt Medical BV, Petten, Holland.

All chemicals were obtained from Sigma Aldrich and buffers were prepared in-house using analytical grade water (unless otherwise noted).

The parent murine antibody m11B6, with specific for the human kallikrein 2, was obtained from the University of Turku, Finland.

m11B6 heavy chain [SEQ ID NO: 23]:
DVQLQESGPGLVKPSQSLSLTCTVTGNSITSDYAWNWIRQFPGNRLE

WMGYISYSGSTTYSPSLKSRFSITRDTSKNQFFLQLNSVTPEDTATY

FCATGYYYGSGFWGQGTLVTVSSAKTTPPSVYPLAPGSAAQTNSMVT

LGCLVKGYFPEPVTVTWNSGSLSSGVHTFPAVLESDLYTLSSSVTVP

SSPRPSETVTCNVAHPASSTKVDKKIVPRDCGCKPCICTVPEVSSVF

IFPPKPKDVLTITLTPKVTCVVVDISKDDPEVQFSWFVDDVEVHTAQ

-continued

TQPREEQFNSTFRSVSELPIMHQDWLNGKEFKCRVNSAAFPAPIEKT

ISKTKGRPKAPQVYTIPPPKEQMAKDKVSLTCMITDFFPEDITVEWQ

WNGQPAENYKNTQPIMNTNGSYFVYSKLNVQKSNWEAGNTFTCSVLH

EGLHNHHTEKSLSHSPGK m11B6 light chain [SEQ ID NO: 24]:
DIVLTQSPASLAVSLGQRATISCRASESVEYFGTSLMHWYRQKPGQP

PKLLIYAASNVESGVPARFSGSGSGTDFSLNIQPVEEDDFSMYFCQQ

TRKVPYTFGGGTKLEIKRTDAAPTVSIFPPSSEQLTSGGASVVCFLN

NFYPKDINVKWKIDGSERQNGVLNSWTDQDSKDSTYSMSSTLTLTKD

EYERHNSYTCEATHKTSTSPIVKSFNRNEC

A humanised counterpart antibody, h11B6, was produced as described in Examples 2 and 3 above (see FIG. 1).

For in vivo studies, the prostate carcinoma cell lines LNCaP expressing hK2 (ATCC, Manassas, Va., USA) and DU145 (ATCC, Manassas, Va., USA) were used. Cells were cultured in RPMI 1640 medium supplemented with 10% fetal bovine serum and PEST (penicillin 100 IU/ml and 100 µg/ml streptomycin). The cells were maintained at 37° C. in a humidified incubator with 5% $CO_2$ and were detached with trypsin-EDTA solution (0.25% trypsin, 0.02% EDTA in buffer, Thermo Scientific). Matrigel matrix from BD-biosciences (San-Jose, Calif., USA) was used when xenografting LNCaP cells. NMRI-Nu, (Charles River) and Balb/c-Nu (in house bread) mice were inoculated with the two cell lines.

Conjugation and Radiolabelling

Conjugation of CHX-A"-DTPA with 11B6:

Solutions of the murine and humanised 11B6 mAbs in PBS was adjusted to pH 9.2 using 0.07 M sodium borate buffer, prior to being concentrated on an Amicon Ultra-2 centrifugal filter (2 ml, 100 K). The resultant protein solution was then conjugated with chelator CHX-A"-DTPA (Macrocyclics, USA) in a molar ratio of 3:1 chelator to antibody at 40° C. The reaction was terminated after 4 h and CHX-A"-DTPA-11B6 (DTPA-11B6) was separated from free chelate by size-exclusion chromatography on a NAP-5 column (GE Healthcare), equilibrated with 20 ml 0.2 M ammonium acetate buffer, pH 5.5. The conjugated 11B6 antibodies were eluted with 1 ml ammonium acetate buffer.

Radiolabeling of DTPA-11B6:

Murine and humanised DTPA-11B6, in ammonium acetate buffer pH 5.5 was mixed with a predetermined amount of $^{177}LuCl_3$. A final activity of 0.5-0.6 MBq per subject was used for biodistribution or a final activity of 18-20MBq per subject was used for SPECT studies. After incubation at room temperature for 2 h, the labeling was terminated and purified on a NAP-5 column, equilibrated with PBS Animal Studies All animal experiments were performed in accordance with national legislation on laboratory animals' protection.

Male immunodeficient nude mice, NMRI-Nu, (6-8 wk old) and Balb/c-Nu, were used for this study. All mice were xenografted with LNCaP cells or DU145 on their left or right flank, 8-10 million cells, in 100 µl growth medium and 100 µl Matrigel.

Biodistribution Studies

Biodistribution studies were performed on both h11B6 and m11B6.

Six groups (n=4) of mice were injected intravenously with either 20 µg of h11B6 or 20 µg m11B6 labeled with $^{177}Lu$.

The animals were sacrificed at 24 h p.i., 48 h p.i and 72 h p.i. and organs of interest were analysed with an automated NaI(Tl) well-counter with a 3-inch NaI (Tl) detector (1480 WIZARD, Wallac Oy, Turku, Finland).

The tissue uptake value, expressed as percent injected dose per gram tissue (% IA/g), was calculated as:

% IA/g=(tissue radioactivity/injected radioactivity)/organ weight×100 wherein for iv injections:

Injected radioactivity=Average radioactivity in control syringes−radioactivity in used syringe−radioactivity in tail The organs were also weighed following dissection.

Kinetic Data

DThe time-% ID curve is represented as a straight line ID(t)=k*t+m up to 48. Based on the data from the second and third time-points (48 respectively 72 h), a mono-exponential curve $(ID(t)=ID(0)e^{-\lambda t})$ is applied for the time interval [48,∞[. If, however, lambda becomes a negative value, i.e. that the ID is increasing between 48 and 72 h, the time ID curve in this time-interval is instead modeled as a straight line, and the pharmaceutical is assumed to be retained in the organ from 72 hours and onwards. To obtain the time-activity curves, the physical half-life is applied.

Note—in some figures, ID is termed "IA"; these expressions are used interchageably herein.

Results

Biodistribution of Humanised $^{177}Lu$-11B6

The biodistribution of $^{177}Lu$-h11B6 is shown in FIG. 5.

The antibody rapidly accumulates in the LNCaP tumour within by 24 hours, and the radioactivity remains high at 72 hours.

Initially, high levels of h11B6 are also evident in the blood and kidneys, which reduce over the following 48 hour period as the antibody is cleared from the body. Such biokinetics are an inevitable and expected consequence of intravenous injection of any radiolabelled antibody.

All other organs, such as bone and muscle, show low levels of radioactivity.

These data demonstrate that $^{177}Lu$-h11B6 can effectively target prostate cancer cells in vivo.

FIG. 6 shows an exemplary SPECT image, in which binding of $^{177}Lu$-h11B6 to LNCaP tumour cells within a xenografted mouse is clearly evident.

$^{17}Lu$-h11B6 Exhibits an Unexpectedly Better Therapeutic Ratio

Comparison of the biodistribution data for humanised $^{177}Lu$-11B6 with that for the parent murine antibody ($^{177}Lu$-m11B6) revealed an unexpected and advantageous difference.

As shown in FIG. 7, uptake of $^{177}Lu$-h11B6 into the LNCaP tumour is elevated by about 20% at 72 post injection compared to $^{177}Lu$-m11B6. Concomitantly, uptake of $^{177}Lu$-h11B6 into healthy bone is reduced by about 40% at 72 post injection compared to $^{177}Lu$-m11B6.

FIG. 8 shows the data expressed as a ratio of antibody uptake in tumour versus healthy bone, at 24, 48 and 72 hours post injection. By 72 hours, this ratio is markedly increased for the humanised 11B6 antibody.

Dosimetry Calculations

Calculation of absorbed doses provides a more sophisticated measure of differences in the kinetics of the humanised antibodies of the invention relative to those of the parent murine 11B6 antibody.

The absorbed dose was calculated according to the MIRD-schema $D(r_T \leftarrow r_S)=\tilde{A}(r_S) \cdot S(r_T \leftarrow r_S)$, where $\tilde{A}$ is the total number of disintegrations in an source organ, and S is the absorbed dose per unit of disintegrations (see Bolch et al., 2009, *J. Nucl. Med.* 50:477-484, the disclosures of which are incorporated herein by reference). The Ã was calculated as the time-integral over the time-activity curve. The S-factor was based on mice-specific Monte Carlo simulations using the Moby-phantom (see Larsson et al., 2011, *Acta Oncol.* 50:973-980 and Keenan et al., 2010, *J. Nucl. Med.* 50:471-476). To get the total absorbed dose, all organs were considered as being source—as well as target sources.

Calculated absorbed dose values for different tissues are shown in Table 6.

TABLE 6

| Organ | Absorbed dose (Gy/MBq) | |
| --- | --- | --- |
|  | m11B6 | h11B6 |
| Blood | 0.915101 | 1.16768 |
| Heart | 1.11217 | 0.756549 |
| Lung | 0.445617 | 0.677907 |
| Liver | 0.2652 | 0.447948 |
| Spleen | 0.396808 | 0.612251 |
| Intestines | 0.189362 | 0.426528 |
| Kidney | 0.291966 | 0.913515 |
| Bone | 0.193169 | 0.179905 |
| Brain | 0.0332977 | 0.0556325 |
| Testes | 0.178707 | 0.516442 |
| Tumour | 1.21858 | 2.20389 |
| Bone (marrow) | 0.309455 | 0.385407 |

As can been seen from Table 6, tumour absorbed dose increases from 1.21 Gy/MBq for m11B6 to 2.2 Gy/MBq for h11B6, i.e. an increase with 80%. The ratios of tumour to bone marrow absorbed doses increases from 3.9 for m11B6 to 5.6 for h11B6 about 40%. Herein, the enhanced therapeutic efficacy for h11B6 compared to m11B6 is shown and indicates that higher absorbed doses to the tumor can be given with less normal organ toxicity.

Antibody Clearance from the Blood

Analysis of blood levels for the humanised and murine 11B6 antibodies is shown in FIG. 10.

The results suggest that h11B6 may be cleared from the blood slightly quicker than the murine 11B6 antibody. If so, such an enhanced clearance rate for the humanised antibody may also be of therapeutic benefit from a safety perspective, potentially allowing higher activities to be administered.

An enhanced clearance rate may also be beneficial for external imaging

Conclusions

The results of this study demonstrate the following:
the humanised 11B6 antibody, $^{177}$Lu-h11B6, effectively targets prostate tumours in vivo;
the humanised 11B6 antibody exhibits an unexpectedly better therapeutic ratio than its parent murine antibody (as determined by the ratio of uptake in tumours to uptake in healthy bone); and
the humanised 11B6 antibody may be cleared from the blood slightly quicker than the murine 11B6 antibody.

Taken together, these findings provide compelling evidence of the enhanced therapeutic efficacy of humanised 11B6 antibodies in the treatment (and diagnosis) of prostate cancer.

Since the humanised and murine antibodies are targeted to the same antigen (namely, human kallikrein 2), the calculated difference in the update ratio in tumour to healthy bone marrow cannot readily be predicted or explained (particularly given that the humanised antibody appears to exhibit a lower affinity for the target hK2 antigen compared to the parent murine antibody; see Example 4).

The difference in the relative uptake in tumour compared to healthy bone between the humanised and murine 11B6 antibodies is of considerable importance since this comparison provides a measure of the therapeutic ratio. A higher value for this ratio (as evident for the humanised 11B6 antibody) is indicative of a better therapeutic antibody. In particular, a higher therapeutic ratio means that higher absorbed doses of therapeutically-radiolabelled h11B6 can be administered to achieve a better therapeutic effect (since binding of the humanised antibody to healthy tissue and organs is much lower than for the murine antibody). The higher ratio also indicates that h11B6 will be better than the murine antibody for diagnostic purposes (since it equates to a lower signal to noise ratio, allowing imaging of smaller tumours including metastases).

In conclusion, the data demonstrate that humanisation of the 11B6 antibody gives an enhanced possibility for early diagnosis and an unexpectedly higher therapeutic efficacy in the treatment prostate cancer.

Example 7—Demonstration of Diagnostic and Therapeutic Efficacy

The aim of this study was to confirm the utility of 11B6, a mAb that specifically targets an epitope inside the catalytic cleft of hK2, as a vehicle to deliver highly toxic radionuclides specifically to the sites of prostate cancer growth. In this proof of concept study, we labelled the parent murine 11B6 antibody with 177Lu, a low energy beta particle that also employs gamma emission, enabling SPECT-imaging to be performed.

Materials & Methods

Materials $^{177}$Lu was purchased from Mallinkrodt Medical BV, Petten, Holland. The Cyclone™ Storage Phosphor System and the OptiQuant™ image analysis software (Perkin Elmer, Wellesley, Mass., USA) was used to measure the radioactivity on the ITLC (instant thin layer chromatography) strips (Biodex, US) for determining labeling kinetics and radiochemical purity. All chemicals were obtained from Sigma Aldrich and the buffers were in-house prepared using analytical grade water if not otherwise noted. The mAb 11B6 is an antibody specific for the human kallikrein 2 with an affinity for this antigen of about 1.2 nM; see FIG. 1 (obtained from the University of Turku, Finland). For the in vivo studies, the prostate carcinoma cell lines LNCaP expressing hK2 (ATCC, Manassas, Va., USA) were used. Cells were cultured in RPM' 1640 medium supplemented with 10% fetal bovine serum and PEST (penicillin 100 IU/ml and 100 µg/ml streptomycin). The cells were maintained at 37° C. in a humidified incubator with 5% $CO_2$ and were detached with trypsin-EDTA solution (0.25% trypsin, 0.02% EDTA in buffer, Thermo Scientific).

Conjugation and Radiolabeling

Conjugation of CHX-A"-DTPA with 11B6:

A solution of the mAb 11B6 in PBS was adjusted to pH 9.2 using 0.07 M sodium borate buffer. The sample was concentrated on an Amicon Ultra-2 centrifugal filter (2 ml, 100 K). The protein solution was conjugated with the chelator CHX-A"-DTPA (Macrocyclics, USA) in a molar ratio of 3:1 chelator to antibody at 40° C. The reaction was terminated after 4 h and CHX-A"-DTPA-11B6, from now on called DTPA-11B6, was separated from free chelate by size-exclusion chromatography on a NAP-5 column (GE Healthcare) equilibrated with 20 ml 0.2 M ammonium acetate buffer, pH 5.5. Conjugated 11B6 and 5A10 was eluted with 1 ml ammonium acetate buffer.

Radiolabeling of DTPA-11B6:

DTPA-11B6 in ammonium acetate buffer pH 5.5 was mixed with a predetermined amount of $^{177}$LuCl$_3$. After incubation at room temperature for 2 h, the labeling was terminated and purified on a NAP-5 column, equilibrated with PBS. Labeling efficiency and labeling kinetics were monitored with ITLC strips, eluted with 0.2 M citric acid. In this system, the radiolabelled conjugate remains at the origin line, while free Lu-177 migrates with the front of the solvent. The radioactivity distribution was determined with a PhosphorImager system (Perkin Elmer, Wellesley, Mass., USA) using the Optiquant as quantification software (Perkin Elmer, Wellesley, Mass., USA).

Animal Studies

All animal experiments were performed in accordance with national legislation on laboratory animals' protection. The animal study has been approved by the local Ethics Committee for Animal Research. Male immunodeficient nude mice, NMRI, (6-8 wk old) purchased from Taconic Europe (Bomholt, Denmark) were used for this study.

Xenografts of hK2-expressing LNCaP prostate carcinoma cells were subcutaneously implanted in the right flank and/or left flank at about 10*10$^6$ cells per injection.

Animals that developed LNCaP tumors were divided into groups and injected with either the therapeutic agent 177Lu-DTP-11B6 or with a control, see Table 7 below:

TABLE 7

| Animals | Group nr | Treatment |
|---|---|---|
| 5 animals/group | 1 | NaCl (control) |
| 11 groups | 2 | Unspecific Ab labeled with 177Lu—low absorbed dose |
| Total = 55 animals | 3 | Unspecific ab labeled with 177Lu—high absorbed dose |
| | 4 | Only 177Lu—low absorbed dose |
| | 5 | Only 177Lu—high absorbed dose |
| | 6 | 177Lu-DTPA-m11B6: A/4 |
| | 7 | 177Lu-DTPA-m11B6: A/2 |
| | 8 | 177Lu-DTPA-m11B6: A |
| | 9 | 177Lu-DTPA-m11B6: 2*A |
| | 10 | 177Lu-DTPA-m11B6: 3*A |
| | 11 | Only m11B6 |

A = 26.7 MBq

All animals included were continuously measured and weighed within an interval of 3-4 days.

Initially some animals got a lower activity (8MBq) of $^{177}$Lu-DTPA-11B6 for investigation of the localization of the therapeutic agent using SPECT. One mouse from group 8 was also studied with SPECT. These animals had their organs removed and an automated NaI(T1) well-counter with a 3-inch NaI (Tl) detector (1480 WIZARD, Wallac Oy, Turku, Finland) was used to quantify radioactivity in these tissue samples.

To study the effect on the bone marrow blood samples (10 µL) were taken regularly. Blood samples were collected twice a week for 8 weeks post-injection and WBC counts, RBC counts, and platelet counts were analyzed in a Medonic Cell Analyzer-Vet CA530 Vet (Boule Medical, Stockholm, Sweden). At the time of blood sampling, the weight and physical condition of the animals were monitored. Toxicity was evaluated by monitoring animals for loss of body weight, decline in general condition, and hematologic toxicity.

Tumor volume was measured with a caliper. The length l, with w and thickness t were measured and the volume was calculated.

Therapy Planning

Based on the relationship between absorbed dose and biological effect on the bone marrow in rats undergoing Radioimmunotherapy with 90Y and 177Lu (see Larsson et al., 2012, Med. Phys. 39(7):4434-43), it could be estimated that the LD50 for bone marrow would be in the order of 12 Gy. In the literature LD50 for acute irradiation of rats and mice are the same, about 9 Gy (for example, see *Radiobiology for the radiologist*, Hall & Giacca (Eds), 2006, 6$^{th}$ edition).

The therapies were then designed from the assumption of a tolerable absorbed dose of 12 Gy to bone marrow. Then, from the dosimetry calculations the activity corresponding to this absorbed dose was calculated.

Corresponding doses/activities were used for the controls.

Results

Animal Tumor Shrinkage

FIG. 11 shows how the tumor in one of the mice (visible on the animal's flank, under the skin) decreases in volume following treatment.

Radioimmunotherapy Results

FIG. 12 shows the results for the study groups with administered activities (a) D, (b) 2×D and (c) a control group (where D=26.7 MBq).

There is a clear trend of decrease of tumor volume in both treatment groups. The onset of tumor shrinkage is seen already a few days after injection of 177Lu-m11B6. In the control group there is an increase of tumor volume after the injection of NaI solution.

FIG. 13(a) shows the results for one of the mice in the group injected with activity A. Here, the tumor grows steadily from day one until day six when activity A of 177Lu-m11B6 is administered. Following treatment, a rapid drop in tumor volume is observed.

In the SPECT study (8 d pi) the tumor volume is shown with still activity present; see FIG. 13(b).

Conclusion

The present study with exemplary antibody 177Lu-m11B6 clearly demonstrates the therapeutic efficacy of hK2-targeted antibodies against prostate cancer tumours in vivo.

Example 8—Therapeutic Efficacy of an Exemplary $^{177}$Lu-Labeled Humanised 11B6 Antibody of the Invention in Prostate Cancer Xenografts Materials & Methods Antibodies, Conjugation and Radiolabeling Antibodies:

The exemplary humanised monoclonal antibody 11B6 (IgG1/kappa, transient expressed in HEK 293 cells), comprising a heavy chain according to SEQ ID NO:12 and a light chain according to SEQ ID NO:13, was provided by Innovagen AB, Lund (1 mg/ml in PBS pH 7.4, Lot No. 90476.30). A non-specific IgG antibody was utilised as an isotype control (IgG antibody from mouse serum, Sigma 1-8765).

Conjugation:

The exemplary h11B6 non-specific IgG control antibody were conjugated with the chelator CHX-A"-DTPA (Macrocyclics, USA) as followed: A solution of the antibody was concentrated on an Amicon Ultra-2 centrifugal filter (2 mL, 100 K) and was later adjusted to pH 9.2 using 0.07 M sodium borate buffer (Sigma Aldrich).

Coupling of the chelator compound CHX-A"-DTPA to the protein solution in a molar ratio of approximately 3:1 (chelator to antibody) was performed similarly to a previously described method (see Almqvist et al). The coupling efficiency, i.e. number of obtained chelators per antibody can be determined by a spectrophotometric method (Pippin et al) but was not analysed in this study. However, the coupling preferably should not exceed 3 chelators/antibody in order to avoid damage to the protein. The chelator was added to the protein and the solution was incubated with gentle shaking at 40° C.

The reaction was terminated after 4 h and CHX-A"-DTPA-h11B6, referred to as DTPA-h11B6, was separated from free chelate by size-exclusion chromatography on a NAP-5 column (GE Healthcare) equilibrated with 20 ml 0.2 M ammonium acetate buffer (Sigma Aldrich), pH 5.5. Conjugated h11B6 was eluted with 1 ml ammonium acetate buffer and aliquoted samples were stored at −20° C.

Conjugation of the IgG control antibody was controlled in the similar way as above.

Radiolabeling:

Conjugated h11B6 or IgG control antibody (typically 200-300 µL of ~1 µg/µL in 0.2 M sodium acetate buffer pH 5.5) was mixed with a predetermined amount (~200-300 MBq) of $^{177}LuCl_3$ (IDB Holland) and incubated at room temperature for 1.5-2 h. After incubation, the labeling was terminated and purified on a NAP-5 column (GE Healthcare), equilibrated with PBS (Thermo Scientific). Labeling efficiency was monitored with instant thin layer chromatography (Biodex, USA), eluted with 0.2 M citric acid (Sigma Aldrich). In this system, the radiolabeled conjugate remains at the origin line, while free $^{177}Lu$ migrates with the front of the solvent. The radioactive distribution was determined with a Cyclone Storage Phosphor System using the Optiquant as quantification software (both from Perkin Elmer).

The radiolabeling of the IgG control antibody was performed in the similar way as above.

Therapy Study

Cell Lines: LNCaP (hK2+) were purchased from American Type Culture Collection (ATCC). Cells were cultured in RPMI 1640 medium (Thermo Scientific) supplemented with 10% fetal bovine serum (Thermo Scientific) with penicillin 100 IU/mL and 100 µg/mL streptomycin (Thermo Scientific). The cells were maintained at 37° C. in a humidified incubator at 5% $CO_2$ and were detached with trypsin-EDTA solution (Thermo Scientific).

All animal experiments were conducted in compliance with the national legislation on laboratory animals' protection, and with the approval of the Ethics Committee for Animal Research (Lund University, Sweden). In-house bred male immunodeficient Balb/c nude mice (6-8 weeks of age) were used. Mice were xenografted with LNCaP cells on their right flank by s.c. injection (8-10 million cells) in 100 µL growth medium and 100 µL Matrigel (BD Matrigel™ Basement Membrane Matrix Growth Factor Reduced, Phenol Red Free, Cat No 356231). Mice with established tumors having a diameter of at least ~3 mm were included in the study and divided into the three groups described below in Table 8. The animals were i.v. injected in the tail vein. The 20 MBq activity-level was chosen because doses at this amount have been used in a study with m11B6, showing good therapeutic effect (see Example 7).

TABLE 8

Three groups of animals were included: One group injected with $^{177}$Lu-h11B6, one with $^{177}$Lu-unsepcific mAb (to show the specificity of h11B6), and one with NaCl (as a control group).

| Group | n  | Treatment           | Activity (MBq) |
|-------|----|---------------------|----------------|
| 1     | 12 | $^{177}$Lu-h11B6    | 20             |
| 2     | 10 | $^{177}$Lu-unspecific mAb | 20       |
| 3     | 10 | NaCl                | —              |

The therapeutic efficacy was assessed by repeated measurement of the tumour size using a caliper. The tumour volume was calculated by measuring the length (L) and the width (W) of the tumor and then calculating the volume V as $0.5 \times L \times W \times W$.

Also, hematological (white blood cell counts, red blood cell counts, platelet number and haemoglobin counts) and weight measurements were taken repeatedly for all animals in order to identify any potential hematological toxicity and to monitor the animals' general condition. The hematological toxicity is especially important to monitor when evaluating radioimmunotherapy since the radioactivity will be distributed in the blood and finally reach the bone marrow, where the blood stem cells are situated.

Mice that developed a tumour length/width exceeding 14 mm, or a weight loss exceeding 15% compared to the initial weight, or otherwise had a negatively affected general condition, or had a combination of all these three parameters, were terminated according to the ethical guidelines.

Results

Assessment of Therapeutic Efficacy

As shown in FIG. 14(a), administration of the exemplary humanised 11B6 antibody of the invention ($^{177}$Lu-h11B6) prevented tumour growth in the mice (and resulted in a pronounced reduction in tumour volume in all but one of the animals tested). In contrast, tumours continued to grow quickly in mice treated with either the IgG control antibody (see FIG. 14b) or NaCl (see FIG. 14c).

The data from the individual animals shown in FIG. 14 is summarized in the form of Kaplan-Meier curves in FIG. 15. Administration of $^{177}$Lu-h11B6 produced a marked increase in the survival rate of the mice over the term of the experiment, with over 80% of the animals still alive upon termination of the experiment 60 days post injection (compared to 0% survival in the two control groups).

Assessment of Hematological Toxicity

Assessment of white blood cell counts, red blood cell counts, platelet number, haemoglobin counts and weight did not reveal any toxicity effect of administration of $^{177}$Lu-h11B6 (data not shown).

Discussion

The results of this study reveal a significant therapeutic effect of $^{177}$Lu-h11B6 treatment in the prostate cancer xenograft model.

The activity administered to the mico (20 MBq) corresponds to an absorbed dose to the bone marrow of approximately 10 Gy, which was well-tolerated by these animals. Even at this low activity of 20 MBq, a large therapeutic effect was observed. As estimated earlier, a tumour absorbed dose of at least 60 Gy can be expected.

No indications of hematological toxicity were observed.

REFERENCES

Almqvist Y., et al. In vitro and in vivo characterization of 177Lu-huA33: a radio-immunoconjugate against colorectal cancer. *Nucl Med Biol.* 2006; 33:991-998.

Pippin C G et al. Spectrophotometric method for the determination of a bifunctional DTPA ligand in DTPA-monoclonal antibody conjugates. *Bioconjug Chem.* 1992; 3:342-5.

Example 9—Radionuclide Therapy Dosimetry Planning and Treatment of Prostate Cancer in a Patient For radionuclide therapy (RNT), the radiation source is distributed in the whole and the radioactivity is normally administered systemically as a radiopharmaceutical. The radioactivity distribution depends on the amount of radiopharmaceutical that accumulates over time in different tissues, something which varies between patients (1).

RNT treatment should be based on a prescribed absorbed dose (2). Then first one should perform a pre-therapy study using a tracer amount of the radiopharmaceutical, and determine the tumor and organ absorbed doses. Usually, this information is expressed as a factor describing the organ absorbed dose per unit administered activity, in units of mGy/MBq; $D^P_T$(organ).

If the therapeutic administration is then given under similar conditions, this factor can be used to determine the activity that needs to be administered in order to deliver a prescribed absorbed dose to a given organ, tissue or tumor (4,6).

In the case of prostate cancer treatment with radiolabelled h11B6 antibodies, a pre-therapy study should be based on $^{111}$In imaging with $^{111}$In-h11B6. $^{111}$In is best suitable for quantitative (planar/SPECT) imaging when then $^{177}$Lu is to be the therapeutic radionuclide. When then the $D^P_T$(organ) is determined the therapy can be given with a therapy activity $A_T$ giving a prescribed therapy effect. During therapy, the activity distribution and corresponding dose rate should be calculated based on imaging to get the actual therapy absorbed dose given to tumor and normal organs, necessary for evaluation of treatment.

In case of therapy where the bone marrow toxicity level is reached as a result of the treatment planning then bone-marrow support is necessary and based on dosimetry calculations for the bone marrow cavity the time for reinfusion of stem cells has to be determined.

In summary, the following treatment scheme should be planned accordingly:

Pre-Therapy Dosimetry Study
1. 111 In-labeled h11B6 (200-300 MBq) injection
2. Blood sampling—activity concentration in blood and plasma determined first week.
3. Imaging (SPECT/Planar) over 1 week (7 times)
4. Organ Dosimetry based on LundaDose scheme (3)
5. Therapy activity determined limited by specified absorbed dose to radiosensitive organs as bone marrow (2-3 Gy), kidneys (20-30 Gy) and liver (12-36 Gy).

Therapy Including Intra-Therapy Dosimetry
1. 177Lu-labeled h11B6 administered (based on pretherapy dosimetry)
2. Blood sampling—activity concentration in blood and plasma
3. Imaging over 1 week (6 times)
4. Organ Dosimetry=>Verification of prescribed therapy absorbed dose.

Specific Comments on Dosimetry

The cumulated activity is the number of decays that occur in a given region over a period of time. The unit is Bq s, or Bq h. When ionizing radiation travels through matter, it interacts and deposits energy. The energy imparted is the sum of all energy deposits in a given volume. The absorbed dose is the ratio of the mean energy imparted and the mass of the volume. The unit of absorbed dose is Gray (Gy), 1 Gy equals 1 J/kg.

From the values of the activity in a tissue at different times, the cumulated activity is determined by integration, and the mean absorbed dose can be determined. Activity measurements are made using planar imaging for whole-organ dosimetry. Quantitative SPECT/CT allows for dosimetry in smaller volumes using voxel-based methods.

From the 3D distribution of activity concentration values, the absorbed dose rate distribution can be calculated using so-called point dose kernels or voxel S values, describing the energy deposition pattern around a point source located in water (or bone). This method assumes that the anatomical region is homogeneous in terms of density, such as soft tissues within the trunk. For body regions where the density is heterogeneous, as in the lungs, a direct Monte Carlo calculation is preferable. Here, the activity distribution from SPECT or PET is used as input to a Monte Carlo dose calculation code.

REFERENCES

1. Strand S-E, Zanzonico P, Johnson T K. Pharmacokinetic modeling. Med Phys 1993; 20(2):515-27
2. ICRU report nr 67—Dose Specifications in Nuclear Medicine. Adelstein S J, DeLuca P, Feinendegen L E, Green L, Howell R W, Humm J L, Strand S E ICRU; 2002
3. The LundADose Method for Planar Image Activity Quantification and Absorbed-Dose Assessment in Radionuclide Therapy. Sjogreen, K., Ljungberg, M., Wingardh, K., Minarik, D., and Strand, S. E. (2005): *Cancer Biother. Radiopharm.,* 20:92-97
4. Quantitative imaging for clinical dosimetry. Bardies M, Flux G, Lassman M, Monsieurs N, Savolainen S, Strand S-E Nucl Instr and Methods 2006:569:467-471.
5. 177Lu-[DOTA0,Tyr3] octreotate therapy in patients with disseminated neuroendocrine tumors: Analysis of dosimetry with impact on future therapeutic strategy. Garkavij Michael, Nickel Mattias, Sjögreen-Gleisner Katarina, Ljungberg Michael, Ohlsson Tomas, Wingårdh Karin, Strand Sven-Erik, Tennvall Jan. Cancer 2010:116(4 Suppl):1084-92.
6. Dosimetry in patients with B-cell lymphoma treated with [(90)Y]ibritumomab tiuxetan or [(131)I]tositumomab Sjögreen-Gleisner K., Dewaraja Y K., Chisea C., Tennvall J., Lindén O., Strand S E, Ljungberg M. Q J Nucl Med Mol Imaging, 2011 April; 55(2):126-54.

The invention claimed is:

1. An antibody polypeptide with binding specificity for human kallikrein-2 (hK2), wherein the antibody polypeptide comprises
   (a) a heavy chain variable region comprising the amino acid sequences of SEQ ID NO:1 and SEQ ID NO:2 and SEQ ID NO:3; and
   (b) a light chain variable region comprising the amino acid sequences of SEQ ID NO:4 and SEQ ID NO:5 and SEQ ID NO:6,
   wherein the heavy chain variable region and light chain variable region comprise framework amino acid sequences from one or more human antibodies, and
   wherein the antibody polypeptide is an intact IgG antibody.

2. An antibody polypeptide according to claim 1 wherein the antibody polypeptide exhibits an enhanced therapeutic ratio compared to the murine 11B6 antibody.

3. An antibody polypeptide according to claim 1 comprising a heavy chain variable region which comprises the amino acid sequence of SEQ ID NO: 8 and a light chain variable region which comprises the amino acid sequence of SEQ ID NO: 9.

4. An antibody polypeptide according to claim 1 comprising a heavy chain constant region which comprises the amino acid sequence of SEQ ID NO: 10 and a light chain constant region which comprises the amino acid sequence of SEQ ID NO: 11.

5. An antibody polypeptide according to claim 1 comprising a heavy chain which consists of the amino acid sequence of SEQ ID NO: 12 and a light chain which consists of the amino acid sequence of SEQ ID NO: 13.

6. An antibody polypeptide according to claim 1 wherein the antibody polypeptide is linked, directly or indirectly, to a therapeutic moiety.

7. An antibody polypeptide according to claim 6 wherein the therapeutic moiety is a cytotoxic moiety that comprises one or more radioisotopes.

8. An antibody polypeptide according to claim 6 wherein the therapeutic moiety is a cytotoxic moiety that comprises one or more cytotoxic drugs.

9. An antibody polypeptide according to claim 1 wherein the antibody polypeptide further comprises a detectable moiety.

10. An antibody polypeptide according to claim 9 wherein the detectable moiety comprises a radioisotope.

11. An antibody polypeptide according to claim 10 wherein the radioisotope is capable of simultaneously acting in a multi-modal manner as a detectable moiety and also as a cytotoxic moiety.

12. A pharmaceutical composition comprising an antibody polypeptide according to claim 1 and a pharmaceutically acceptable excipient, diluent or carrier.

13. A method for the treatment or diagnosis of prostate cancer in a patient, the method comprising the step of administering an effective amount of an antibody polypeptide according to claim 1.

14. A method according to claim 13 wherein the prostate cancer to be treated is non-localised prostate cancer.

15. A method according to claim 13 wherein the prostate cancer to be treated is metastatic prostate cancer.

16. A method according to claim 15 wherein the metastatic prostate cancer to be treated is metastases of the lymph system; metastases of the bone; or metastasis within the pelvis, rectum, bladder or urethra.

17. A method according to claim 13 wherein the prostate cancer to be treated is castration-resistant prostate cancer (CRPC).

18. A method according to claim 13 wherein radioguided surgery is performed on the patient following administration of the antibody polypeptide in order to remove prostate cancer cells.

\* \* \* \* \*

UNITED STATES PATENT AND TRADEMARK OFFICE
CERTIFICATE OF CORRECTION

| | |
|---|---|
| PATENT NO. | : 10,100,125 B2 |
| APPLICATION NO. | : 15/036170 |
| DATED | : October 16, 2018 |
| INVENTOR(S) | : Par Oskar Vilhelmsson Timmermand et al. |

It is certified that error appears in the above-identified patent and that said Letters Patent is hereby corrected as shown below:

In the Specification

Under Column No. 7, Line no. 63, Replace:
"DIVLTQSPDSLAVSLGERATINCIKASESVEYFGTSLMHWYQQKP"
With:
-- DIVLTQSPDSLAVSLGERATINCKASESVEYFGTSLMHWYQQKP --

Signed and Sealed this
Twentieth Day of December, 2022

Katherine Kelly Vidal
*Director of the United States Patent and Trademark Office*

SEQUENCE LISTING

<160> NUMBER OF SEQ ID NOS: 24

<210> SEQ ID NO 1
<211> LENGTH: 6
<212> TYPE: PRT

<213> ORGANISM: Artificial Sequence
<220> FEATURE:
<223> OTHER INFORMATION: Mutated murine antibody derived sequence

<400> SEQUENCE: 1

Ser Asp Tyr Ala Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Mutated murine antibody derived sequence

<400> SEQUENCE: 2

Tyr Ile Ser Tyr Ser Gly Ser Thr Thr Tyr Asn Pro Ser Leu Lys Ser
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Mutated murine antibody derived sequence

<400> SEQUENCE: 3

Gly Tyr Tyr Tyr Gly Ser Gly Phe
1               5

<210> SEQ ID NO 4
<211> LENGTH: 15
<212> TYPE: PRT
<213> ORGANISM: Artificial Sequence
<220> FEATURE:
<223> OTHER INFORMATION: Mutated murine antibody derived sequence

<400> SEQUENCE: 4

Lys Ala Ser Glu Ser Val Glu Tyr Phe Gly Thr Ser Leu Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Mutated murine antibody derived sequence

<400> SEQUENCE: 5

Ala Ala Ser Asn Arg Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Mutated murine antibody derived sequence

<400> SEQUENCE: 6

Gln Gln Thr Arg Lys Val Pro Tyr Thr
1               5

<210> SEQ ID NO 7
<211> LENGTH: 261
<212> TYPE: PRT
<213> ORGANISM: Homo sapiens
<220> FEATURE:
<223> OTHER INFORMATION: hK2 sequence

<400> SEQUENCE: 7

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro
            260

<210> SEQ ID NO 8
<211> LENGTH: 117
<212> TYPE: PRT
<213> ORGANISM: Artificial Sequence
<220> FEATURE:
<223> OTHER INFORMATION: Mutated murine antibody derived sequence

<400> SEQUENCE: 8

Gln Val Gln Leu Gln Glu Ser Gly Pro Gly Leu Val Lys Pro Ser Asp
1               5                   10                  15

Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Ser Thr Tyr Tyr Asn Pro Ser Leu
    50                  55                  60

Lys Ser Arg Val Thr Met Ser Arg Asp Thr Ser Lys Asn Gln Phe Ser

```
                65                  70                  75                  80
Leu Lys Leu Ser Ser Val Thr Ala Val Asp Thr Ala Val Tyr Tyr Cys
                    85                  90                  95

Ala Thr Gly Tyr Tyr Tyr Gly Ser Gly Phe Trp Gly Gln Gly Thr Leu
                100                 105                 110

Val Thr Val Ser Ser
            115

<210> SEQ ID NO 9
<211> LENGTH: 111
<212> TYPE: PRT
<213> ORGANISM: Artificial Sequence
<220> FEATURE:
<223> OTHER INFORMATION: Mutated murine antibody derived sequence

<400> SEQUENCE: 9

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
                20                  25                  30

Gly Thr Ser Leu Met His Trp Tyr Gln Gln Lys Pro Gly Gln Pro Pro
            35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys
                100                 105                 110

<210> SEQ ID NO 10
<211> LENGTH: 330
<212> TYPE: PRT
<213> ORGANISM: Artificial Sequence
<220> FEATURE:
<223> OTHER INFORMATION: Mutated murine antibody derived sequence

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 107
<212> TYPE: PRT
<213> ORGANISM: Artificial Sequence
<220> FEATURE:
<223> OTHER INFORMATION: Mutated murine antibody derived sequence

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 447
<212> TYPE: PRT
<213> ORGANISM: Artificial Sequence
<220> FEATURE:
<223> OTHER INFORMATION: Mutated murine antibody derived sequence

<400> SEQUENCE: 12

Gln Val Gln Leu Gln Glu Ser Gly Pro Gly Leu Val Lys Pro Ser Asp
1               5                   10                  15
```

```
Thr Leu Ser Leu Thr Cys Ala Val Ser Gly Asn Ser Ile Thr Ser Asp
            20                  25                  30

Tyr Ala Trp Asn Trp Ile Arg Gln Pro Pro Gly Lys Gly Leu Glu Trp
            35                  40                  45

Ile Gly Tyr Ile Ser Tyr Ser Gly Ser Thr Thr Tyr Asn Pro Ser Leu
 50                  55                  60

Lys Ser Arg Val Thr Met Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Thr Gly Tyr Tyr Gly Ser Gly Phe Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
     210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
     290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430
```

His Asn His Tyr Thr Gln Lys Ser Leu Ser Leu Ser Pro Gly Lys
            435                 440                 445

<210> SEQ ID NO 13
<211> LENGTH: 218
<212> TYPE: PRT
<213> ORGANISM: Artificial Sequence
<220> FEATURE:
<223> OTHER INFORMATION: Mutated murine antibody derived sequence

<400> SEQUENCE: 13

Asp Ile Val Leu Thr Gln Ser Pro Asp Ser Leu Ala Val Ser Leu Gly
1               5                   10                  15

Glu Arg Ala Thr Ile Asn Cys Lys Ala Ser Glu Ser Val Glu Tyr Phe
            20                  25                  30

Gly Thr Ser Leu Met His Trp Tyr Gln Gln Lys Pro Gly Gln Pro Pro
        35                  40                  45

Lys Leu Leu Ile Tyr Ala Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Thr Arg
                85                  90                  95

Lys Val Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 14
<211> LENGTH: 351
<212> TYPE: DNA
<213> ORGANISM: Artificial Sequence
<220> FEATURE:
<221> NAME/KEY: source
<222> LOCATION: 1..351
<223> OTHER INFORMATION: /mol_type="unassigned DNA"
      /note="Nucleic acid molecule encoding antibody polypeptide"
      /organism="Artificial Sequence"

<400> SEQUENCE: 14
caggttcagc tgcaggaaag cggacctggc ttggtgaaac ccagcgatac ccttagcctg      60
acatgtgctg tgtctggcaa ttccatcact tccgactatg cgtggaactg gattcggcaa     120
ccaccgggaa aagggctcga gtggataggg tacatcagct attctggttc aaccacgtac     180
aatccctcac tgaagagtag ggttaccatg tccagagaca cctccaagaa ccagttcagc     240
ctgaagctga gtagtgtgac agccgtagat acagccgtct attactgcgc aacagggtac     300

```
tactatggct ctggcttttg gggtcaagga actctcgtca ctgtgtcaag c        351
```

```
<210> SEQ ID NO 15
<211> LENGTH: 333
<212> TYPE: DNA
<213> ORGANISM: Artificial Sequence
<220> FEATURE:
<221> NAME/KEY: source
<222> LOCATION: 1..333
<223> OTHER INFORMATION: /mol_type="unassigned DNA"
      /note="Nucleic acid molecule encoding antibody polypeptide"
      /organism="Artificial Sequence"

<400> SEQUENCE: 15
gacatagtgc tcactcagag ccctgatagc ttggctgtca gtcttgggga aagagccacc    60
atcaactgca aagcgtccga aagcgtcgag tatttcggga ctagcctgat gcactggtat   120
cagcagaaac ccggacaacc gcctaagctg ctgatctatg cagcctctaa tcgcgaaagt   180
ggcgttccag acaggttttc cggttctgga tcaggcacag acttcaccct cacgatttcc   240
tcactgcaag ctgaggatgt agccgtgtac tactgtcagc agacacggaa agtgccctac   300
acctttggtc agggcacaaa gctggagatt aag                               333
```

```
<210> SEQ ID NO 16
<211> LENGTH: 10
<212> TYPE: PRT
<213> ORGANISM: Artificial Sequence
<220> FEATURE:
<223> OTHER INFORMATION: Forward primer

<400> SEQUENCE: 16

Asp Ile Val Leu Thr Gln Ser Pro Ala Ser
1               5                   10
```

```
<210> SEQ ID NO 17
<211> LENGTH: 10
<212> TYPE: PRT
<213> ORGANISM: Artificial Sequence
<220> FEATURE:
<223> OTHER INFORMATION: Forward primer

<400> SEQUENCE: 17

Asp Val Gln Leu Gln Glu Ser Gly Pro Gly
1               5                   10
```

```
<210> SEQ ID NO 18
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Forward primer"
      /organism="Artificial Sequence"
<220> FEATURE:
<221> NAME/KEY: misc_feature
<222> LOCATION: 42
<223> OTHER INFORMATION: Wherein n is A, T, C or G

<400> SEQUENCE: 18
ttactcgcgg cccagccggc catggcggay athgtrytva ncartctcc              50
```

```
<210> SEQ ID NO 19
<211> LENGTH: 34
<212> TYPE: DNA
<213> ORGANISM: Artificial Sequence
```

<220> FEATURE:
<221> NAME/KEY: source
<222> LOCATION: 1..34
<223> OTHER INFORMATION: /mol_type="unassigned DNA"
    /note="Reverse primer"
    /organism="Artificial Sequence"

<400> SEQUENCE: 19
gcgccgtcta gaattaacac tcattcctgt tgaa                                34

<210> SEQ ID NO 20
<211> LENGTH: 51
<212> TYPE: DNA
<213> ORGANISM: Artificial Sequence
<220> FEATURE:
<221> NAME/KEY: source
<222> LOCATION: 1..51
<223> OTHER INFORMATION: /mol_type="unassigned DNA"
    /note="Reverse primer"
    /organism="Artificial Sequence"

<400> SEQUENCE: 20
gatacagttg gtgcagcatc ggtccgtttt atttccagct tggtcccccc t             51

<210> SEQ ID NO 21
<211> LENGTH: 52
<212> TYPE: DNA
<213> ORGANISM: Artificial Sequence
<220> FEATURE:
<221> NAME/KEY: source
<222> LOCATION: 1..52
<223> OTHER INFORMATION: /mol_type="unassigned DNA"
    /note="Forward primer"
    /organism="Artificial Sequence"

<400> SEQUENCE: 21
tgctgctggc ggccgctcca gccatggctg aygtvcarct kcaggagtcd gg            52

<210> SEQ ID NO 22
<211> LENGTH: 38
<212> TYPE: DNA
<213> ORGANISM: Artificial Sequence
<220> FEATURE:
<221> NAME/KEY: source
<222> LOCATION: 1..38
<223> OTHER INFORMATION: /mol_type="unassigned DNA"
    /note="Rverse primer"
    /organism="Artificial Sequence"

<400> SEQUENCE: 22
cgccaccaga gctctcacaa tccctgggca caattttc                            38

<210> SEQ ID NO 23
<211> LENGTH: 441
<212> TYPE: PRT
<213> ORGANISM: Mus <mouse, genus>
<220> FEATURE:
<223> OTHER INFORMATION: m11B6 heavy chain

<400> SEQUENCE: 23

Asp Val Gln Leu Gln Glu Ser Gly Pro Gly Leu Val Lys Pro Ser Gln
1               5                   10                  15

Ser Leu Ser Leu Thr Cys Thr Val Thr Gly Asn Ser Ile Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Ser Tyr Ser Gly Ser Thr Thr Tyr Ser Pro Ser Leu

```
            50                  55                  60
Lys Ser Arg Phe Ser Ile Thr Arg Asp Thr Ser Lys Asn Gln Phe Phe
 65                  70                  75                  80

Leu Gln Leu Asn Ser Val Thr Pro Glu Asp Thr Ala Thr Tyr Phe Cys
                     85                  90                  95

Ala Thr Gly Tyr Tyr Tyr Gly Ser Gly Phe Trp Gly Gln Gly Thr Leu
                100                 105                 110

Val Thr Val Ser Ser Ala Lys Thr Thr Pro Pro Ser Val Tyr Pro Leu
                115                 120                 125

Ala Pro Gly Ser Ala Ala Gln Thr Asn Ser Met Val Thr Leu Gly Cys
                130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Glu Ser
                165                 170                 175

Asp Leu Tyr Thr Leu Ser Ser Ser Val Thr Val Pro Ser Ser Pro Arg
                180                 185                 190

Pro Ser Glu Thr Val Thr Cys Asn Val Ala His Pro Ala Ser Ser Thr
                195                 200                 205

Lys Val Asp Lys Lys Ile Val Pro Arg Asp Cys Gly Cys Lys Pro Cys
210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
                260                 265                 270

Val Asp Asp Val Glu Val His Thr Ala Gln Thr Gln Pro Arg Glu Glu
                275                 280                 285

Gln Phe Asn Ser Thr Phe Arg Ser Val Ser Glu Leu Pro Ile Met His
                290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Pro Lys Glu Gln Met
                340                 345                 350

Ala Lys Asp Lys Val Ser Leu Thr Cys Met Ile Thr Asp Phe Phe Pro
                355                 360                 365

Glu Asp Ile Thr Val Glu Trp Gln Trp Asn Gly Gln Pro Ala Glu Asn
370                 375                 380

Tyr Lys Asn Thr Gln Pro Ile Met Asn Thr Asn Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
                420                 425                 430

Lys Ser Leu Ser His Ser Pro Gly Lys
                435                 440

<210> SEQ ID NO 24
<211> LENGTH: 218
<212> TYPE: PRT
<213> ORGANISM: Mus <mouse, genus>
```

```
<220> FEATURE:
<223> OTHER INFORMATION: m11B6 light chain

<400> SEQUENCE: 24

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Phe
            20                  25                  30

Gly Thr Ser Leu Met His Trp Tyr Arg Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile Gln
65                  70                  75                  80

Pro Val Glu Glu Asp Asp Phe Ser Met Tyr Phe Cys Gln Gln Thr Arg
                85                  90                  95

Lys Val Pro Tyr Thr Phe Gly Gly Gly Thr Lys Leu Glu Ile Lys Arg
            100                 105                 110

Thr Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```